US009516245B2

(12) United States Patent
Yokohama

(10) Patent No.: US 9,516,245 B2
(45) Date of Patent: Dec. 6, 2016

(54) ENDOSCOPE APPARATUS

(71) Applicant: OLYMPUS CORPORATION, Tokyo (JP)

(72) Inventor: Tomohiro Yokohama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 221 days.

(21) Appl. No.: 14/536,904

(22) Filed: Nov. 10, 2014

(65) Prior Publication Data

US 2015/0138328 A1    May 21, 2015

Related U.S. Application Data

(63) Continuation of application No. PCT/JP2013/063158, filed on May 10, 2013.

(30) Foreign Application Priority Data

May 16, 2012    (JP) .................................. 2012-112677

(51) Int. Cl.
H04N 5/351        (2011.01)
H04N 5/235        (2006.01)
(Continued)

(52) U.S. Cl.
CPC ........... H04N 5/351 (2013.01); A61B 1/00018 (2013.01); A61B 1/045 (2013.01); G02B (Continued)

(58) Field of Classification Search
CPC ............... H04N 5/2353; H04N 5/351; H04N 2005/2255; H04N 5/343; H04N 5/3454; H04N 5/372; H04N 5/3765
See application file for complete search history.

(56) References Cited

U.S. PATENT DOCUMENTS

2009/0021628 A1*    1/2009    Tamakoshi ........... H04N 5/3728
                                                                                    348/311

FOREIGN PATENT DOCUMENTS

JP    62-059473 A    3/1987
JP    04-227175 A    8/1992
(Continued)

OTHER PUBLICATIONS

International Search Report dated Aug. 20, 2013 issued in PCT/JP2013/063158.
(Continued)

*Primary Examiner* — Andy Rao
*Assistant Examiner* — Tyler Edwards
(74) *Attorney, Agent, or Firm* — Scully, Scott, Murphy & Presser, P.C.

(57) ABSTRACT

An endoscope apparatus includes: e.g., an image pickup device including an effective pixel region and an ineffective pixel region, a signal transmission cable that transmits an output signal from the image pickup device, an analog front-end circuit that samples the transmitted output signal and converts a resulting output signal into a digital signal, and a timing generator that generate first and second image pickup drive signals for driving the image pickup device in first and second image pickup device drive modes using horizontal transfer clocks having different frequencies, respectively, and when the first image pickup device drive mode is switched to the second image pickup device drive mode, a control circuit adjusts a timing for a timing generator to generate the second image pickup drive signal.

17 Claims, 18 Drawing Sheets

(51) Int. Cl.

| | |
|---|---|
| *G02B 21/00* | (2006.01) |
| *A61B 1/00* | (2006.01) |
| *A61B 1/045* | (2006.01) |
| *H04N 5/343* | (2011.01) |
| *H04N 5/345* | (2011.01) |
| *H04N 5/372* | (2011.01) |
| *H04N 5/376* | (2011.01) |
| *G02B 23/24* | (2006.01) |
| *A61B 1/05* | (2006.01) |
| *H04N 5/225* | (2006.01) |

(52) U.S. Cl.
CPC . *21/0084* (2013.01); *H04N 5/2353* (2013.01); *H04N 5/343* (2013.01); *H04N 5/3454* (2013.01); *H04N 5/372* (2013.01); *H04N 5/3765* (2013.01); *A61B 1/051* (2013.01); *G02B 23/2476* (2013.01); *H04N 2005/2255* (2013.01)

(56) References Cited

FOREIGN PATENT DOCUMENTS

| | | |
|---|---|---|
| JP | 08-084299 A | 3/1996 |
| JP | 3312766 B2 | 8/2002 |
| JP | 2005-110867 A | 4/2005 |
| JP | 2009-017459 A | 1/2009 |
| JP | 4608766 B2 | 1/2011 |
| JP | 2012-065899 A | 4/2012 |

OTHER PUBLICATIONS

English Abstract of corresponding JP 06-285017 dated Oct. 11, 1994.

English Abstract of corresponding JP 2002-165141 dated Jun. 7, 2002.

* cited by examiner

FIG. 2
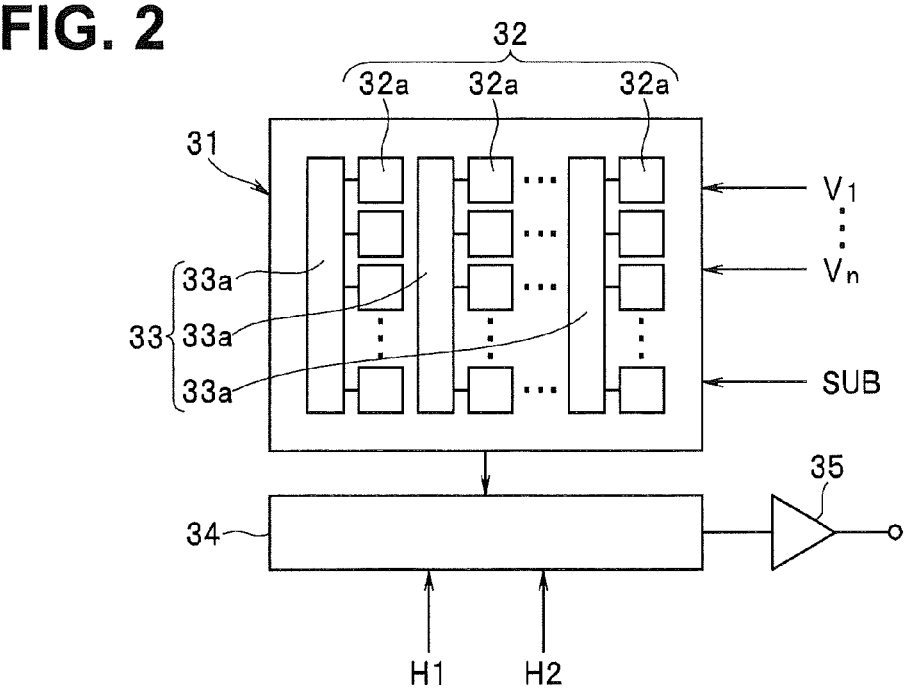
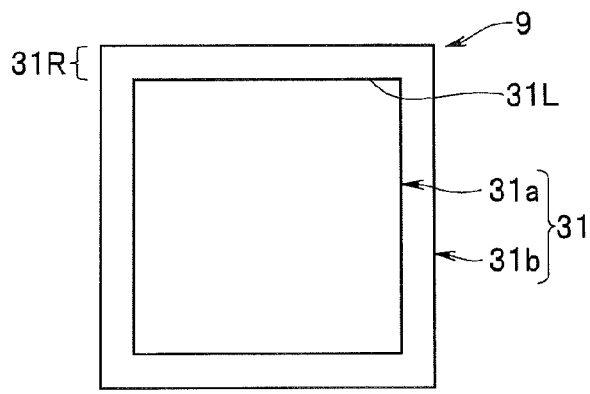
FIG. 3 (A)
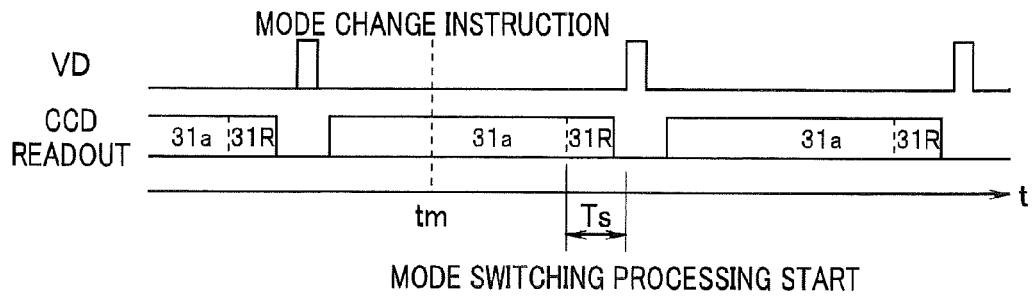
FIG. 3 (B)

---- CCD OUTPUT WAVEFORM
—— AFE INPUT WAVEFORM

→ TIME

FIG. 14

| EXPOSURE INFORMATION | | INSERTION PORTION LENGTH | |
|---|---|---|---|
| SHUTTER SPEED | AGC GAIN | <=5000mm | >5000mm |
| =1/60sec | >10dB | FIRST DRIVE MODE | SECOND DRIVE MODE |
| =1/60sec | <=10dB | FIRST DRIVE MODE | FIRST DRIVE MODE |
| =1/60sec | MINIMUM GAIN | FIRST DRIVE MODE | FIRST DRIVE MODE |
| <1/60sec | MINIMUM GAIN | FIRST DRIVE MODE | FIRST DRIVE MODE |

FIG. 16

| DISTAL END PORTION ACCELERATION | DRIVE MODE |
|---|---|
| <0.1G | SECOND DRIVE MODE |
| >=0.1G | FIRST DRIVE MODE |

FIG. 18

| BLURRING | DRIVE MODE |
|---|---|
| NO | SECOND DRIVE MODE |
| YES | FIRST DRIVE MODE |

ENDOSCOPE APPARATUS

CROSS REFERENCE TO RELATED APPLICATION

This application is a continuation application of PCT/JP2013/063158 filed on May 10, 2013 and claims benefit of Japanese Application No. 2012-112677 filed in Japan on May 16, 2012, the entire contents of which are incorporated herein by this reference.

BACKGROUND OF THE INVENTION

1. Field of the Invention

The present invention relates to an endoscope apparatus including an image pickup device and a signal processing circuit for the image pickup device.

2. Description of the Related Art

In recent years, endoscopes with an image pickup device mounted in a distal end of an insertion portion thereof have widely been used in the medical field and the industrial field. Also, the image pickup devices mounted in the endoscopes have the tendency of pixel count increase to have a large number of pixels.

As described above, an image pickup device with an increased number of pixels requires an increase in drive frequency of a horizontal transfer signal, etc., in image pickup drive signals for reading out information on an image picked up by the image pickup device, in order to maintain a same frame rate as that before the increase.

For example, as a first conventional example, Japanese Patent Publication No. 3312766 discloses an endoscope apparatus including a signal processing apparatus including a plurality of image pickup device drive circuits and a plurality of signal processing circuits corresponding to plural types of image pickup devices, in which an image pickup device drive circuit and a signal processing circuit corresponding to an image pickup device mounted in an endoscope connected to the signal processing apparatus are selected.

Also, as a second conventional example, Japanese Patent Publication No. 4608766 discloses that in a camera mounting in an image pickup device, a frame rate of the image pickup device is changed according to a detected brightness and a detected frequency of illumination.

SUMMARY OF THE INVENTION

An endoscope apparatus according to an aspect of the present invention includes: an image pickup device including an effective pixel region to be used for display and an ineffective pixel region not to be used for display, in order to pick up an image of an object; a signal transmission cable disposed inside an insertion portion, the signal transmission cable transmitting an output signal of the image pickup device; an analog front-end circuit that receives an input of the output signal of the image pickup device transmitted via the signal transmission cable, and samples the output signal and converts a resulting output signal into a digital signal; a signal processing circuit that performs signal processing on the output signal of the image pickup device inputted via the analog front-end circuit, and outputs a first horizontal transfer clock having a predetermined frequency and a second horizontal transfer clock having a frequency that is different from the frequency of the first horizontal transfer clock; a timing generator that in order to read out information in the effective pixel region of the image pickup device in an image pickup device drive mode that is either of two different first and second image pickup device drive modes, receives an input of either the first horizontal transfer clock or the second horizontal transfer clock, and upon receipt of an input of the first horizontal transfer clock, generates a first image pickup drive signal based on the first horizontal transfer clock in the first image pickup device drive mode, and upon receipt of an input of the second horizontal transfer clock, generates a second image pickup drive signal based on the second horizontal transfer clock in the second image pickup device drive mode; and a control circuit that controls operation of the timing generator and the signal processing circuit, and when the image pickup device drive mode for reading out the information in the effective pixel region of the image pickup device is switched from the first image pickup device drive mode to the second image pickup device drive mode, the control circuit performs control so that a change is made to the frequency of the second horizontal transfer clock for the timing generator to generate the second image pickup drive signal during a period from a start of transfer of pixel information in the ineffective pixel region of the image pickup device after completion of transfer of pixel information in the effective pixel region of the image pickup device until an output of a next vertical synchronization signal, and then output the vertical synchronization signal.

BRIEF DESCRIPTION OF THE DRAWINGS

FIG. 2 is a diagram illustrating a schematic configuration of an image pickup device;

FIG. 3(A) illustrates an effective pixel region and an ineffective pixel region of the image pickup device, and FIG. 3(B) is a diagram illustrating a period in which a mode change is actually made in response to an operation to provide a mode change instruction;

FIG. 14 is a diagram illustrating a table that is a typical example of the content of a table for selecting a drive mode according to a cable length and exposure information;

FIG. 16 is a diagram illustrating a table that is a typical example of the content of a table for selecting a drive mode according to a detected acceleration of a distal end portion;

FIG. 18 is a diagram illustrating a table that is a typical example of the content of a table for selecting a drive mode according to a detected blurring amount of an image.

DETAILED DESCRIPTION OF THE PREFERRED EMBODIMENTS

Embodiments of the present invention will be described below with reference to the drawings.

First Embodiment

Figure 1:
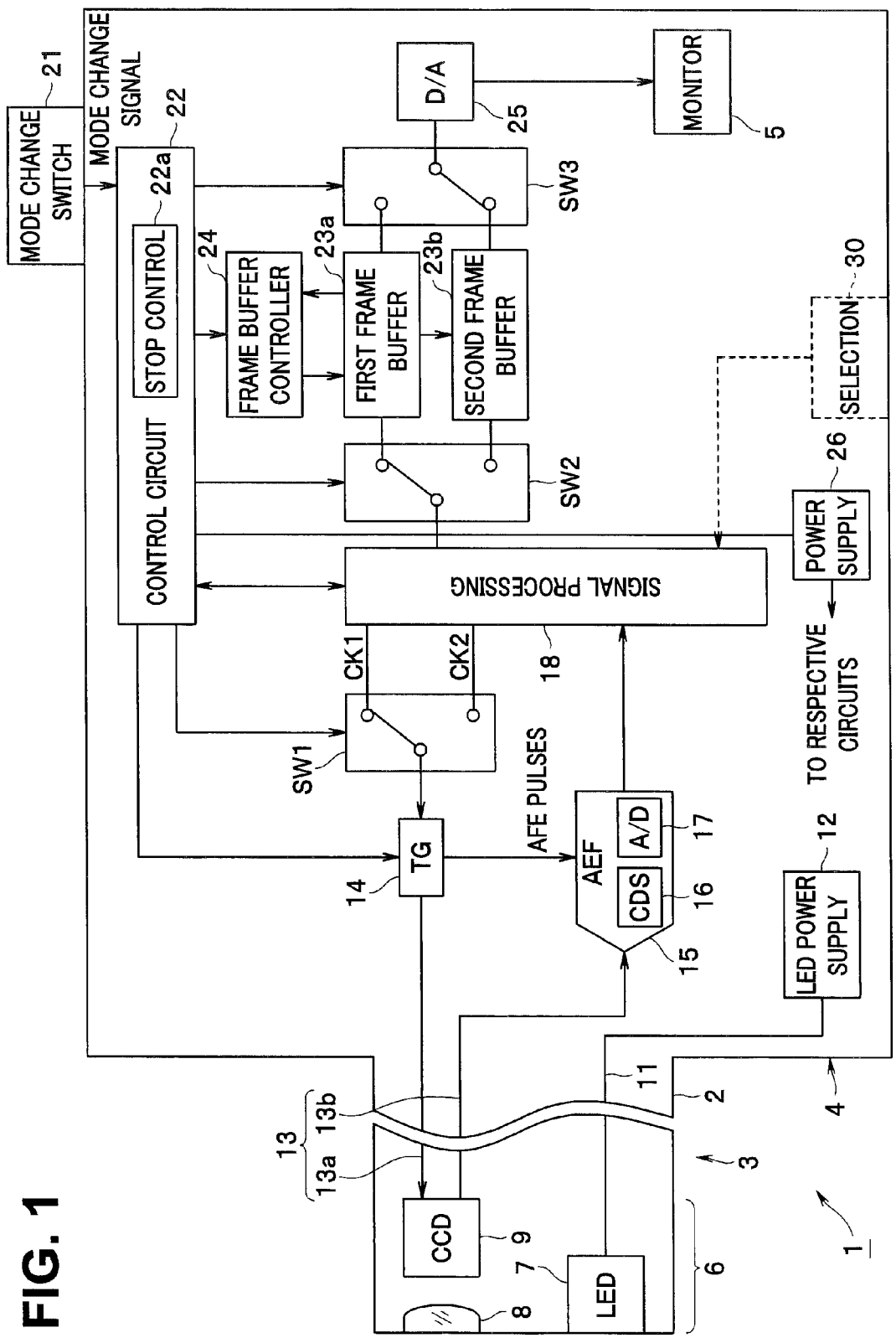
FIG. 1 is a diagram illustrating an overall configuration of an endoscope apparatus according to a first embodiment of the present invention.

As illustrated in FIG. 1, an endoscope apparatus 1 according to a first embodiment of the present invention includes an endoscope 3 including an elongated insertion portion 2, an endoscope apparatus main body portion (hereinafter simply abbreviated as "main body portion") 4, to which the rear end side of the endoscope 3 is integrally or detachably connected, and a monitor 5 integrally or detachably connected to the main body portion 4.

In the endoscope 3, an illumination window via which illumination light is emitted and an image pickup window (observation window) via which an illuminated object is picked up are provided at a distal end portion 6 of the insertion portion 2, and a light-emitting diode (abbreviated as "LED") 7 that emits white light is attached to the illumination window and an objective lens 8 is attached to the image pickup window, and at a position at which the objective lens 8 forms an image, a charge-coupled device (abbreviated as "CCD") 9 is arranged as an image pickup device.

The LED 7 is connected to a LED power supply 12 inside the main body portion 4 via a drive wire 11 inserted in the insertion portion 2, and emits light upon LED drive power supply outputted from the LED power supply 12, whereby white light is emitted from the illumination window to illuminate an object.

Furthermore, an optical image of the illuminated object is formed on an image pickup surface of the CCD 9 via the objective lens 8. The CCD 9 is connected to a timing generator (abbreviated as "TG") 14 that generates CCD drive signals, which is arranged in the main body portion 4 via a signal wire 13a in a signal cable 13 inserted in the insertion portion 2, and is also connected to an analog front-end (abbreviated as "AFE") 15 arranged in the main body portion 4 via a signal wire 13b in the signal cable 13.

The AFE 15 incorporates a correlated double sampling circuit (abbreviated as "CDS circuit"; "CDS" in FIG. 1) 16 that extracts signal components in the CCD 9 from an output signal of the CCD 9, and an analog-digital conversion circuit (abbreviated as "A/D conversion circuit"; "A/D" in FIG. 1) 17 that converts analog signal components sampled by the CDS circuit 16 into a digital image signal. Note that an analog signal generated by the CDS circuit 16 using sampling is amplified by an AGC circuit, which is a gain-variable amplifier, to a signal having a fixed amplitude and then converted by the A/D conversion circuit 17 into a digital signal. As will be described later, a first drive mode and a second drive mode provide different amplitudes to an output signal of the CCD 9, and thus, the output signal is amplified by the AGC circuit in order to obtain an image (video image) of a same brightness even when the drive mode is changed to the other.

The TG 14 outputs sampling pulses (abbreviated as "SPs") for extracting image signal components in the output signal of the CCD 9 to the CDS circuit 16, and A/D conversion pulses for performing A/D conversion to the A/D conversion circuit 17, as AFE pulses.

The digital image signal resulting from the conversion by the A/D conversion circuit 17 is inputted to a signal processing circuit 18.

The signal processing circuit 18 performs signal processing on the digital image signal outputted from the AFE 15 in order to covert the digital image signal to a video signal (image signal) to be displayed on the monitor 5, which is display means (e.g., perform color separation processing for color separation, white balance processing, gamma processing and contour enhancement processing on the output signal of the CCD 9). Note that a signal processing circuit may be defined as one including components of reference numerals 18, SW2, 23a, 23b, SW3 and 25 in FIG. 1. The signal processing circuit in this case performs signal processing on an output signal of the AFE 15 to generate a video signal (image signal) to be displayed on the monitor 5.

Furthermore, in the present embodiment, a mode change switch 21 for changing drive modes (also simply referred to as "mode(s)") is provided so that the CCD 9 can be driven at two different drive frequencies. By operating the mode change switch 21 to provide an instruction, a user can provide a change instruction for a drive mode change from an operating state in the first drive mode to operation in the second drive mode, and provides a mode change instruction for the other way around, i.e., a mode change from an operating state in the second drive mode to operation in the first drive mode.

A mode change signal provided by operating the mode change switch 21 is inputted to a control circuit 22 that controls operation of the main body portion 4. Upon an input of the mode change signal, the control circuit 22 controls operation of, e.g., the TG 14 and the signal processing circuit 18 in the main body portion 4 so as to operate according to the mode change.

Also, in the present embodiment, the signal processing circuit 18 outputs first horizontal transfer clocks CK1 and second horizontal transfer clocks CK2 from first and second output ends to the TG 14 via a first switching switch (hereinafter abbreviated as "first switch") SW1 so that the TG 14 can generate CCD drive signals according to the first and second CCD drive modes. Note that the first horizontal transfer clocks CK1 are set to have a high frequency so that CCD drive signals for generating an image with a high frame rate can be generated, and the second horizontal transfer clocks CK2 are set to have a low frequency so that CCD drive signals for generating an image with high image quality can be generated.

The TG 14 outputs CCD drive signals according to the first drive mode or the second drive mode to the CCD 9, using the first horizontal transfer clocks CK1 or the second horizontal transfer clocks CK2 selectively inputted via the first switch SW1.

Note that although FIG. 1 illustrates a configuration in which the signal processing circuit 18 includes a clock generating circuit that generates first horizontal transfer clocks CK1 and second horizontal transfer clocks CK2, a configuration in which the clock generating circuit is provided outside the signal processing circuit 18 may be employed.

In this case, also, the control circuit 22 controls switching of the first switch SW1 to selectively output the first horizontal transfer clocks CK1 and the second horizontal transfer clocks CK2 outputted from the clock generating circuit, to the TG 14. Note that the first horizontal transfer clocks CK1 and the second horizontal transfer clocks CK2 are inputted to the control circuit 22 from the signal processing circuit 18 and the control circuit 22 performs the control operation in synchronization with the first horizontal transfer clocks CK1 or the second horizontal transfer clocks CK2.

As illustrated in FIG. 1, the first switch SW1 is normally set by the control circuit 22 so as to output first horizontal transfer clocks CK1 to the TG 14. Upon an operation to provide a mode change instruction being performed, the control circuit 22 performs a flip of the first switch SW1 so as to output second horizontal transfer clocks CK2 to the TG 14. Also, upon an operation to provide another mode change instruction being performed after the switching of the state to the state in which second horizontal transfer clocks CK2 are outputted to the TG 14, the control circuit 22 switches the position of the first switch SW1 to the other again so as to output first horizontal transfer clocks CK1 to the TG 14.

The image signal subjected to the signal processing in the signal processing circuit 18 is stored in a first frame buffer 23a or a second frame buffer 23b via a second switch SW2. Note that for the first frame buffer 23a and the second frame buffer 23b, a frame buffer controller 24 performs operation to control writing to the frame buffers 23a and 23b and reading from the frame buffers 23a and 23b.

Furthermore, the image signal written in the first frame buffer 23a or the second frame buffer 23b is outputted to a D/A conversion circuit 25 via a third switch SW3. The D/A conversion circuit 25 converts the digital image signal into an analog image signal and outputs the analog image signal to the monitor 5. On a display surface of the monitor 5, an optical image formed on the image pickup surface of the CCD 9 is displayed as an endoscopic image. Also, in the main body portion 4, a power supply circuit 26 that supplies power for making the respective circuits, etc., in the main body portion 4 operate is provided.

FIG. 2 illustrates an image pickup surface 31 and a region around a signal output unit of the CCD 9. The image pickup surface 31 of the CCD 9 includes a light receiving unit 32 with light receiving elements 32a that form pixels to perform photoelectric conversion regularly arranged in horizontal and vertical directions. Furthermore, the image pickup surface 31 includes an interline-type vertical transfer unit 33 including vertical transfer column units 33a extending vertically between the respective light receiving elements 32a and 32a adjacent to one another in the horizontal direction. Note that although the interline-type vertical transfer unit 33 is illustrated here, the same is applicable to a frame transfer-type vertical transfer unit 33.

Also, at a bottom portion of the vertical transfer unit 33, a horizontal transfer unit 34 that receives an input of transferred signal charges at the bottom portion of the vertical transfer unit 33 is formed and at an end portion on the output side of the horizontal transfer unit 34, an amplifier 35 that outputs an output signal of the CCD 9 from the horizontal transfer unit 34 is provided.

Figure 6:
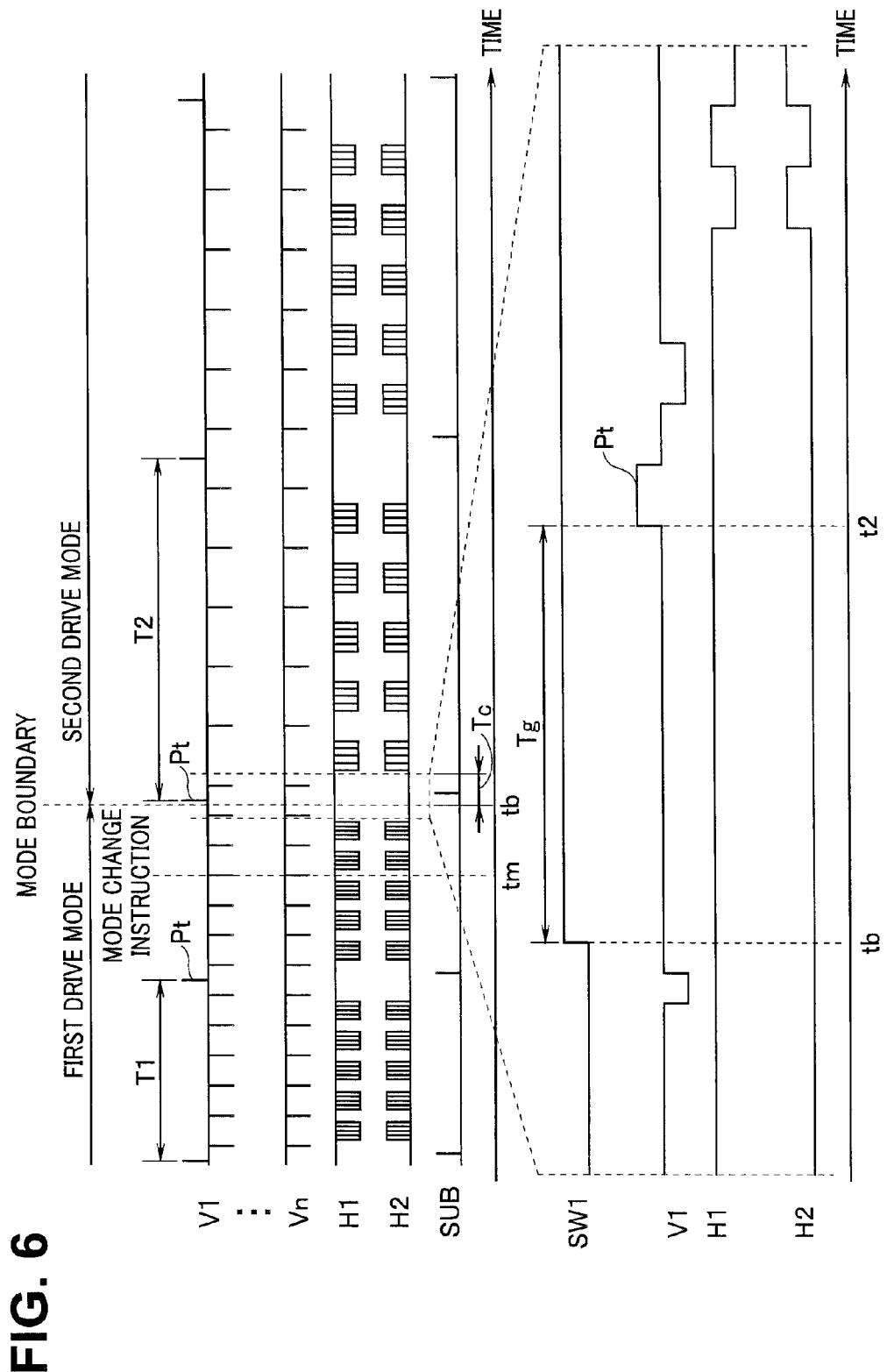
FIG. 6 is a timing chart of operation to, upon provision of an instruction for a mode change, make the mode change near an end of a frame of an image in which the mode change instruction was provided.

Vertical transfer pulses V1, . . . , Vn, which are illustrated in FIG. 2, are applied to the vertical transfer unit 33 side and, e.g., horizontal transfer pulses H1 and H2 are applied to the horizontal transfer unit 34. Furthermore, the signal charges accumulated in the light receiving unit 32 are transferred to the vertical transfer unit 33 by means of application of readout pulses Pt, which are illustrated in FIG. 6.

Also, as illustrated in FIG. 3(A), the image pickup surface 31 includes an effective pixel region 31a (which is an effective pixel region in the light receiving unit 32) used when an endoscopic image (also simply referred to as "image") is displayed on the monitor 5, and an ineffective pixel region 31b (which is an ineffective pixel region in the light receiving unit 32) formed outside the effective pixel region 31a, which is not used for image display. Note that signals in the ineffective pixel region 31b can be used for setting black levels of effective pixels.

The signal charges generated as a result of image pickup by the light receiving unit 32 of the image pickup surface 31 and transferred to the vertical transfer unit 33 are sequentially read out from the left side to the right side along a first horizontal line that is the first from the bottom, that is, the lowest in FIG. 3, then along a second horizontal line that is the second from the bottom and next along a third horizontal line, by means of application of a CCD drive signal. When signal charges are finally read out along a horizontal line that is the top has been read out in such a manner as described above, readout of an image in one frame is completed. Note that an image in each frame is read out immediately after an output of a vertical synchronization signal ("VD" in FIG. 3(B)), in synchronization with the vertical synchronization signal. In other words, an image in each frame is read out between an output of a vertical synchronization signal immediately before a start of readout of the image and an output of a next vertical synchronization signal. The present embodiment will be described in terms of a case where images are sequentially (that is, not interlace scan) read out frame by frame from the CCD 9, which is an image pickup device.

In the present embodiment, as will be described later, upon provision of a mode change instruction, processing for the mode change instruction is performed during a period after a timing of completion of readout of a last horizontal line 31L in the effective pixel region 31a for an image in a frame in which the mode change instruction was provided (that is, during a period of time in which signal readout is performed for an ineffective pixel region 31R that is the upper side of the horizontal line 31L in FIG. 3(A)) and before an output of a next vertical synchronization signal.

As described above, control is performed so that upon an input to provide a mode change instruction, substantial processing in the ineffective pixel region 31b for the mode change instruction is performed so as to smoothly display an image subjected to the mode change, with image disturbance during the image mode change reduced (or suppressed).

FIG. 3(B), which is on the lower side of FIG. 3(A), illustrates a timing chart of operation in this case. In a one-frame period between adjacent vertical synchronization signals ("VD" in FIG. 3(B)), as described in the part below the "VD", signals of pixels in the effective pixel region 31a and, e.g., the ineffective pixel region 31R (in the ineffective pixel region 31b) of the CCD 9 are read out for each frame. Note that in FIG. 3(B), parts of ineffective pixel region 31b other than the ineffective pixel region 31R are omitted.

Then, for example, upon provision of a mode change instruction at a time tm, the control circuit 22 performs control so that actual mode change (mode switching) processing is performed in a period Ts from a start of readout of the ineffective pixel region 31R until an output of a next vertical synchronization signal after readout of the effective pixel region 31a for the relevant frame. As described above, mode switching processing is performed during readout of the ineffective pixel region 31R, preventing occurrence of problems due to displacement of a pixel position to be read out and/or sharp change in image signal level caused by the mode change signal as will be described later with reference to, e.g., FIGS. 5(A) and (B).

Since the insertion portion 2 illustrated in FIG. 1 is considerably long particularly in the industrial field, waveform deterioration occurs when an output signal of the CCD 9 is transmitted using the signal wire 13b forming a transmission path for transmitting the output signal of the CCD 9.

In the present embodiment, the CCD 9 can be driven in the first drive mode and the second drive mode, and for example, in the first drive mode, the TG 14 generates first CCD drive signals with a high drive frequency so that a moving object can be displayed as a smooth movie. In other words, since signal charges in the light receiving unit 32 of the CCD 9 are read out via the CCD drive signals with a high drive frequency, a movie can be displayed at a high frame rate. Note that a frame rate is a value obtained by a total number of pixels included in the light receiving unit 32 of the CCD 9 being divided by a frequency of a horizontal transfer signal in the CCD drive signals, which is indicated by horizontal transfer pulses H1 and H2, which are illustrated in FIG. 6, used for readout of the respective pixels.

On the other hand, in the second drive mode, for putting importance on the image quality, the TG 14 generates second CCD drive signals with a low drive frequency that is lower than that in the first drive mode (that is, a lower frame rate) so that a high-quality image can be displayed.

Figure 4:
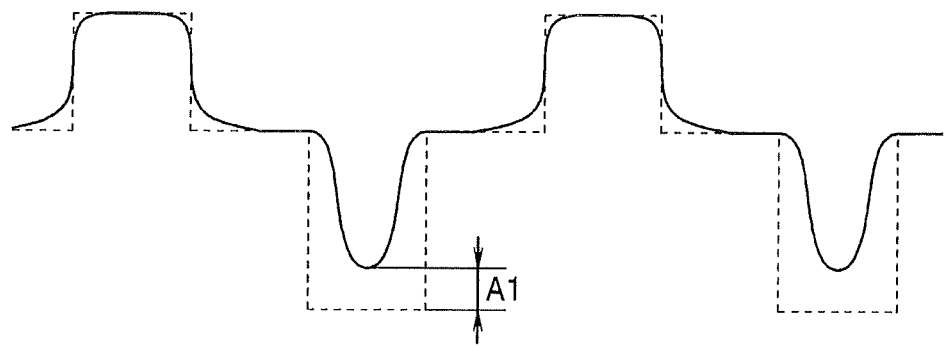
FIGS. 4(A) and 4(B) are diagrams illustrating waveforms of signals inputted to an analog front end when the image pickup device is driven by a first drive mode CCD drive signal and a second drive mode CCD drive signal.
Figure 4:
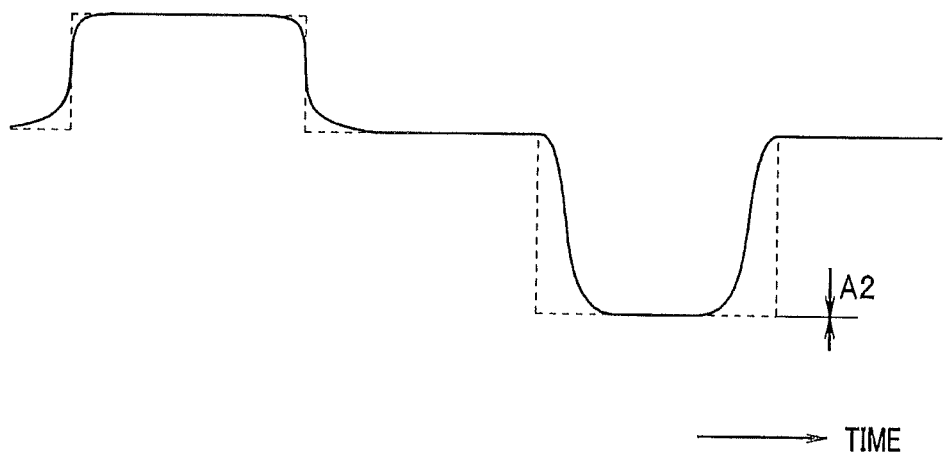

FIGS. 4(A) and 4(B) illustrate an output signal waveform when an output signal of the CCD 9 is transmitted using the signal wire 13b in the first drive mode and the second drive mode, respectively. Note that in FIGS. 4(A) and (B), the horizontal axis represents time, and the vertical axis represents signal level.

The output signal of the CCD 9 has an angular signal waveform reflecting an original signal waveform when the signal was outputted, which is indicated by the dotted line, but because of the long signal wire 13b, the waveform (AFE input waveform) inputted to the AFE 15 via the signal wire 13b becomes a dull waveform, which is indicated by the solid line, due to, e.g., capacity components in the signal wire 13b.

In the case of FIG. 4(A), since the horizontal transfer signal has a high frequency (drive frequency), the AFE input waveform has a large attenuation amount A1 from the CCD 9 output waveform.

On the other hand, in the case of FIG. 4(B), since the horizontal transfer signal has a low frequency in comparison with the case in FIG. 4(A), the AFE input waveform has a small attenuation amount A2 from the CCD 9 output waveform. In FIG. 4(B), the attenuation amount A2 is nearly zero.

Thus, in the second drive mode, signal waveform attenuation caused by the signal wire 13b that transmits an output signal of the CCD 9 can be reduced, and even if noise is mixed in the signal wire 13b, a high-quality signal with a good S/N ratio compared to that in the first drive mode can be inputted to the AFE 15 in the main body portion 4.

Then, where a video signal to be displayed on the monitor 5 is generated by the signal processing circuit 18 through the AFE 15, a high-quality image with a good S/N can be displayed on the monitor 5 as a result of reduction of the signal waveform attenuation caused by the signal wire 13b.

In the present embodiment, normally, an object is displayed in the form of a movie, and thus, in order to smoothly display a moving object by means of the first drive mode, the CCD 9 is driven in the first drive mode that provides a high frame rate or a horizontal transfer signal with a high frequency (drive frequency), and signal processing on the output signal of the CCD 9 is performed.

If a user wishes to obtain high-quality display, the user operates the mode change switch 21, whereby the control circuit 22 performs control so that CCD 9 is driven in the second drive mode that provides a frame rate that is lower than that in the first drive mode or a horizontal transfer signal with a frequency that is lower than that in the first drive mode and signal processing on an output signal of the CCD 9 is performed. Then, as described above, a high-quality endoscopic image can be displayed on the monitor 5.

Also, although a mode change instruction can be provided at an arbitrary timing during the first drive mode, in order to reduce disturbance of an image displayed at the time of the mode change, in the present embodiment, a CCD drive signal change for the mode change is substantially performed in a period near an end of a frame of the image in which the mode change was provided.

Figure 5:
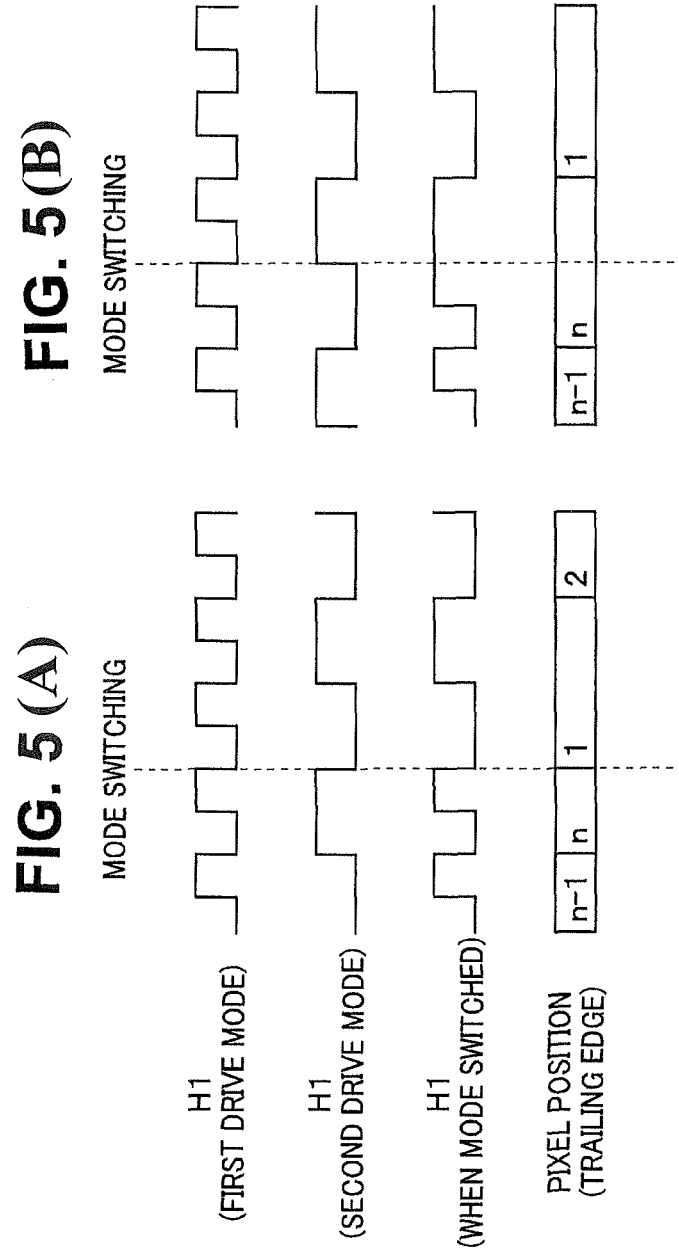
FIGS. 5(A) and 5(B) are diagrams indicating that disturbance of an image occurs if mode switching is performed at the timing when an instruction for a mode change (switching) is provided.

For example, if CCD drive signals are changed to the other in synchronization with a timing for a mode change instruction, as illustrated in FIGS. 5(A) and 5(B), a pixel position that is n in the first drive mode is changed to 1 in the second drive mode, resulting in disturbance of the image.

Here, FIG. 5(A) illustrates horizontal transfer pulses H1 (in the third row) in a case where a mode change (mode switching) instruction is provided at a timing of a trailing edge of a waveform of a horizontal transfer pulse H1 in the first drive mode when horizontal transfer pulses H1 (in the first row) in the first drive mode and horizontal transfer pulses H1 (in the second row) in the second drive mode having a cycle that is twice that of the horizontal transfer pulses H1 in the first drive mode are synchronized with each other and the first drive mode is switched to the second drive mode in synchronization with the instruction, as well as corresponding pixel positions (in the fourth row).

Here, FIG. 5(B) indicates that image disturbance occurs if a horizontal transfer pulse H1 in the first drive mode (in the first row) and a horizontal transfer pulse H1 in the second drive mode (in the second row) are opposite to each other in phase, relative to the case of FIG. 5(A).

In order to avoid image disturbance such as illustrated in FIGS. 5(A) and (B), in the present embodiment, as illustrated in FIG. 6, if a timing of a mode change instruction takes place, the mode is changed to the second drive mode designated by the mode change instruction after a postponement of the mode change until an end of one frame of an image in which the timing of the mode change instruction takes place is close.

Note that in FIG. 6, the first to fifth rows indicate vertical transfer pulses V1, . . . , Vn, horizontal transfer pulses H1 and H2 and charge sweep-away pulses (abbreviated as SUB), which are included in the CCD drive signals for driving the CCD 9, and FIG. 6 also illustrates an enlargement of a period Tc near a mode boundary at which processing is switched to the other for a mode change on the lower side of the first to fifth rows.

Note that in FIG. 6, the horizontal axis represents time, and the vertical axis represents H and L levels of each signal. In the enlarged diagram on the lower side of FIG. 6, which illustrates an enlargement of the period Tc, switching of the first switch SW1, and vertical transfer pulses V1 and horizontal transfer pulses H1 and H2.

As illustrated in FIG. 6, in the first drive mode, the TG 14 applies the CCD drive signals to CCD 9 in units of a frame period T1. The TG 14 generates a readout pulse Pt at a beginning of a frame period T1 to make charges in the light receiving unit 32 be transferred to the vertical transfer unit 33, and immediately after that, generates a charge sweep-away pulse SUB to reset (sweep away) the charges in the light receiving unit 32.

Subsequently, the TG 14 applies vertical transfer pulses V1, . . . , Vn and horizontal transfer pulses H1 and H2 to the CCD 9 to make the signal charges resulting from light reception by the light receiving unit 32 and photoelectric conversion be outputted from the horizontal transfer unit 34 via the amplifier 35, as an output signal of the CCD 9.

Then, upon provision of a mode change instruction at the time tm indicated in FIG. 6, the control circuit 22 performs control so that the state in the first drive mode is maintained until an end of the relevant frame is close, and (processing for) the mode change instruction is postponed (also referred to "wait") until an end of readout of the effective pixel region in the frame, and before an output of a first vertical synchronization signal for a next frame, the first switch SW1 is switched at a time tb as illustrated in the enlarged diagram.

Note that although the example illustrated in FIG. 6 indicates a case where processing for a mode change is started at the time tb, which is a timing after an end of readout (transfer) of a last pixel in the effective pixel region in an image in a frame in which an instruction for the mode change was provided, as illustrated in FIG. 3(B), the processing may be performed during a period Ts from a start of readout of pixels in the ineffective pixel region 31R after completion of all the pixels in the effective pixel region 31a until an output of a next vertical synchronization signal. In other words, the processing for the mode change is performed (started) during a period Ts after an end of readout (transfer) of the last pixel in the effective pixel region in the frame in which the instruction for the mode change was provided until an output of a next vertical synchronization signal, which is a synchronization signal immediately before readout of an image for a next frame.

If the first switch SW1 is at an L level in FIG. 6, the first switch SW1 outputs first horizontal transfer clocks CK1 from the signal processing circuit 18 to the TG 14 as illustrated in FIG. 1, and if the first switch SW1 is switched to an H level, outputs second horizontal transfer clocks CK2 to the TG 14.

Upon an input of the second horizontal transfer clocks CK2, the TG 14 starts operation to generate CCD drive signals for the second drive mode, using the second horizontal transfer clocks CK2.

As illustrated in the enlarged diagram in FIG. 6, from the time tb to a time t2 after a TG startup time period Tg, the TG 14 enters a state in which the TG 14 can output CCD drive signals for the second drive mode. Then, the TG 14 generates a vertical synchronization signal (not illustrated in FIG. 6), a first readout pulse Pt for the second drive mode and a first vertical transfer pulse V1 for the second drive mode, at the time t2.

After the generation of the first vertical transfer pulse V1, the TG 14 also outputs horizontal transfer pulses H1 and H2 for the second mode.

Also, the control circuit 22 switches the second switch SW2 from a state before the switching, reads out signal charges transferred from the light receiving unit 32 to the vertical transfer unit 33 via the first readout pulse Pt, as an image signal from the CCD 9 via a second CCD drive signal, and writes the read-out image signal to a frame buffer connected as a result of the switching. Consequently, the signal charges resulting from light reception in the light receiving unit 32 in a frame period T1 in which a mode change instruction was provided is read out from the CCD 9 via the CCD drive signals for the second drive mode during a frame period T2.

Note that the control circuit 22 performs switching of the third switch SW3 in synchronization with the switching of the second switch SW2 to read out an image signal written before the switching from the frame buffer and display the image signal on the monitor 5.

Then, after the passage of the one-frame period T2, the control circuit 22 switches the second switch SW2 and the third switch SW3 to the other, respectively. As a result of the switching of the third switch SW3, a first image signal written in the second mode is read out from the frame buffer and displayed on the monitor 5. Subsequently, operation that is similar to that of the first drive mode (however, is different in frame rate and frame cycle from those of the first drive mode) is repeated in the second drive mode.

The endoscope apparatus 1 configured as described above includes: the CCD 9, which is an image pickup device including an effective pixel region 31a to be used for display and an ineffective pixel region 31b not to be used for display, in order to pick up an image of an object; the signal cable 13, which is a signal transmission cable disposed inside the insertion portion 2, the signal transmission cable transmitting an output signal of the image pickup device; one analog front-end circuit 15 that receives an input of the output signal of the image pickup device transmitted via the signal transmission cable, and samples the output signal and converts a resulting output signal into a digital signal; the signal processing circuit 18 that performs signal processing on the output signal of the image pickup device inputted via the analog front-end circuit 15; one timing generator 14 that generates first and second image pickup drive signals for selectively driving the image pickup device in first and second image pickup device drive modes for driving the image pickup device using first and second horizontal transfer clocks having different frequencies, respectively; and the control circuit 22 that controls operation of the timing generator 14 and the signal processing circuit 18, and when the first image pickup device drive mode is switched to the second image pickup device drive mode, the control circuit 22 performs control so that a change is made to the frequency of the second horizontal transfer clock for the timing generator 14 to generate the second image pickup drive signals during a period from a start of transfer of pixel information in the ineffective pixel region 31b after completion of transfer of pixel information in the effective pixel region 31a of the image pickup device until an output of a vertical synchronization signal, which is a synchronization signal for a next frame, and then output the vertical synchronization signal.

In the present embodiment, the one timing generator 14 includes one image pickup drive signal generating circuit that generates the first image pickup drive signals and the second image pickup drive signals according to the first horizontal transfer clocks CK1 and the second horizontal transfer clocks CK2, respectively, and one pulse generating circuit that outputs analog front-end pulses to the AFE 15, which is an analog front-end circuit. Also, the one AFE 15 in the present embodiment includes one analog front-end circuit that samples the output signal of the CCD 9, which is the image pickup device driven by the first image pickup drive signals, and the output signal of the image pickup device driven by the second image pickup drive signals, respectively, and converts the respective output signals into digital signals, using the analog front-end pulses.

Note that as in, e.g., a second embodiment, which will be later, the timing generator may include first and second timing generators TG 14a and 14b, and as in the third embodiment, the analog front-end circuit may include first and second AFEs 15a and 15b.

Figure 7:
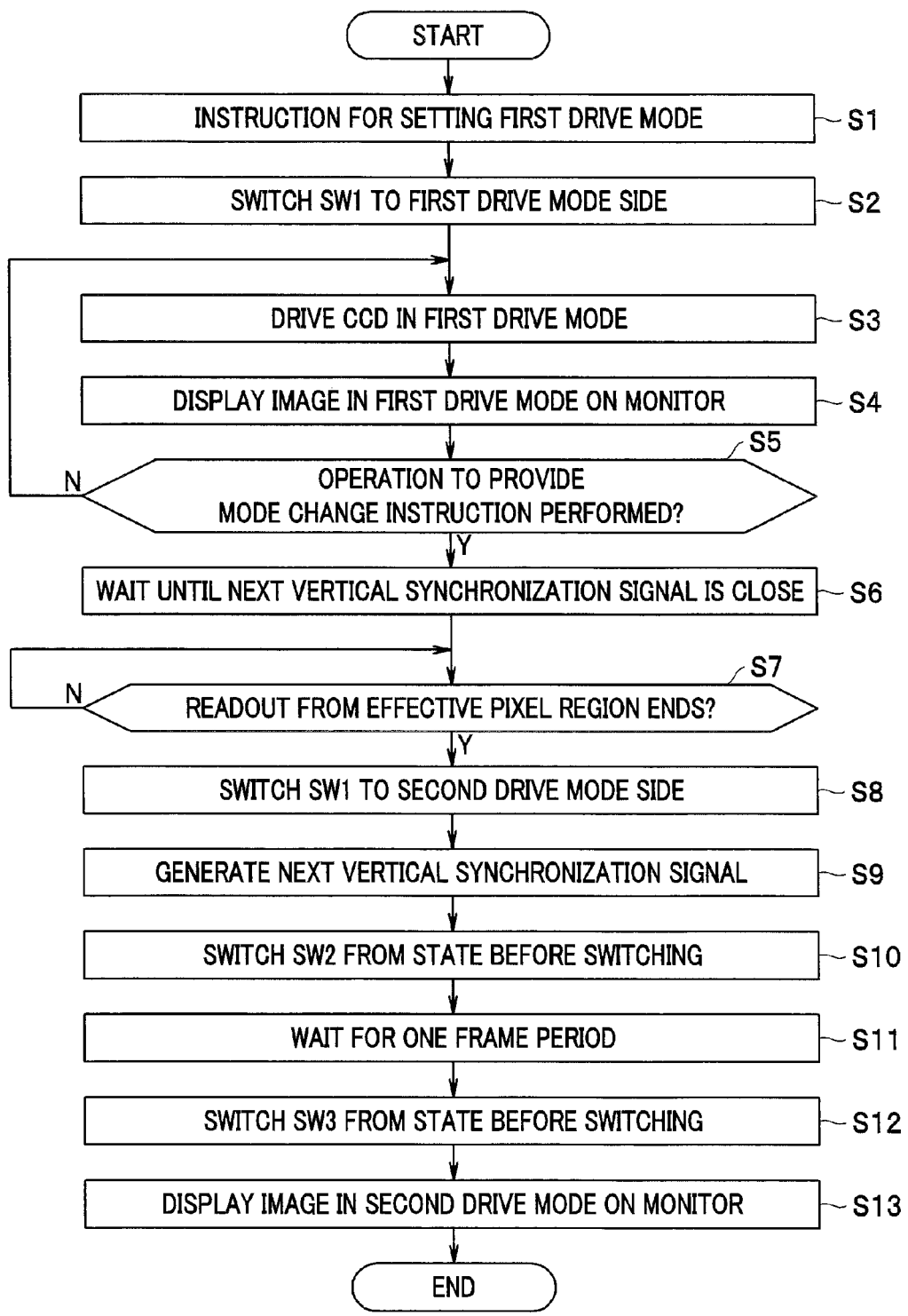
FIG. 7 is a flowchart illustrating typical processing when a mode change instruction is provided in the first embodiment.

Next, operation of the present embodiment will be described with reference to FIG. 7. FIG. 7 illustrates a flowchart indicating typical processing in the present embodiment.

In order to examine the inside of an examination target object, which is an object/subject, by means of the endoscope apparatus 1 illustrated in FIG. 1, the endoscope apparatus 1 is powered on and the insertion portion 2 of the endoscope 3 is inserted into the examination target object. In this case, as illustrated in FIG. 7, in first step 1, a user performs an operation to provide an instruction for setting the first drive mode.

Note that a setting for making the control circuit 22 operate in the first drive mode may be made by a default setting in the endoscope apparatus 1. As indicated in step S2, in response to the instruction for setting the first drive mode, the control circuit 22 sets the first switch SW1 to the first drive mode side as illustrated in FIG. 1. Then, signal processing circuit 18 outputs first horizontal transfer clocks CK1 to the TG 14 via the first switch SW1.

As indicated in step S3, the TG 14 generates first CCD drive signals including horizontal transfer pulses H1 and H2 having a frequency that is equal to that of the first horizontal transfer clocks CK1, based on the first horizontal transfer clocks CK1, to drive the CCD 9. Also, the TG 14 outputs AFE pulses to the AFE 15 to drive the AFE 15. The AFE 15 samples an output signal of the CCD driven by the CCD drive signals for the first drive mode, subjects the output signal to A/D conversion and outputs the resulting signal to the signal processing circuit 18.

As indicated in step S4, the signal processing circuit 18 performs signal processing on the digital image signal outputted from the AFE 15 to display an endoscopic image (simply abbreviated as "image") in a case where the CCD 9 is driven in the first drive mode, on the monitor 5.

The image signal outputted from the signal processing circuit 18 is written in the first frame buffer 23a via the second switch SW2. Note that in a frame in which the image signal is being written in the first frame buffer 23a, the image signal written one frame before in the other second frame buffer 23b is read out and outputted to the monitor 5 via the D/A conversion circuit 25. Then, as described above, the image is displayed on the monitor 5.

The left side of FIG. 6 indicates a timing chart of CCD drive signals when the CCD 9 is driven in the first drive mode.

Also, the output signal of the CCD 9 has a waveform such as illustrated in FIG. 4(A), which is subject to the effect of attenuation caused by the signal wire 13b; however, the horizontal transfer pulses H1 and H2 have a high frequency, enabling a highly-responsive image that smoothly displays even a moving object at a high frame rate to be displayed on the monitor.

Also, as indicated in step S6, the control circuit 22 monitors whether or not an operation to provide a mode change instruction is provided. If no operation to provide a mode change instruction is performed, the operation returns to step S3, the operation in the first drive mode continues.

In the first drive mode, the user can observe a smooth image even in the case of a moving object image; however, if the user wishes to observe the image with high quality in order to observe a site of interest in more detail, the user may operate the mode change switch 21.

If the user operates the mode change switch 21 to provide a mode change instruction, the mode change switch 21 outputs a mode change signal to the control circuit 22. FIG. 6 indicates a case where an operation to provide a mode change instruction is performed at the time tm. The control circuit 22 does not immediately perform mode change processing, but as illustrated in step S6, waits until a next vertical synchronization signal is close. In other words, the mode change processing is postponed until a time near an end of a frame period in which an image (signal) for one frame that is being read out from the CCD 9 in which the operation to provide the mode change instruction was provided.

Then, as indicated in step S7, the control circuit 22 determines whether or not the readout of the effective pixel region 31a has ended (has been completed) in the frame period for the image (signal) that is being read out from the CCD 9 after the operation to provide the mode change operation was performed. The control circuit 22 determines a timing of an end of the readout of the effective pixel region 31a from, for example, a count value of a non-illustrated counter that counts the number of first horizontal transfer clocks CK1. The control circuit 22 performs the processing in step S7 until an end (completion) of the readout of the effective pixel region 31a.

Then, upon an end (completion) of the readout of the effective pixel region 31a, as indicated in step S8, the control circuit 22 switches the first switch SW1 to the second drive mode side (second horizontal transfer clock CK2 side).

A period during which a start of this switching is allowed is indicated by Ts in FIG. 3(B).

As a result of the switching of the first switch SW1, the TG 14 receives inputs of second horizontal transfer clocks CK2 for the second drive mode, and the TG 14 starts operation to generate CCD drive signals for the second drive mode, based on the horizontal transfer clocks CK2.

Then, as indicated in step S9, the TG 14 generates (produces) and outputs a next vertical synchronization signal. Also, as indicated in step S10, the control circuit 22 performs control to switch the second switch SW2 to change a state before the switching.

If the state before the switching is, for example, the state illustrated in FIG. 1, the control circuit 22 performs control to switch the second switch SW2 so as to select the second frame buffer 23b to write an image signal outputted from the signal processing circuit 18 in the second frame buffer 23b.

Note that the control circuit 22 also performs control to switch the third switch SW3 to change the state before the switching.

As indicated in step S11, the control circuit 22 waits until an end of writing of an image signal for one frame in the second frame buffer 23b. Then, upon an end of the writing of the image signal for one frame, as indicated in step S12, the control circuit 22 performs control to switch the third switch SW3 to read out the image signal written in the second frame buffer 23b. Then, as indicated in step S13, an image in the second drive mode is displayed on the monitor 5. Subsequently, operation that is similar to that in the first drive mode is repeated.

Consequently, the mode change processing illustrated in FIG. 7 ends. Subsequently, operation that is similar to that in the first drive mode is repeated. Note that in the second drive mode, if an operation to provide a mode change instruction is further performed, the above-described operation that is, however, operation corresponding to that with the first drive mode replaced by the second drive mode is performed in such a manner as described above.

The present embodiment in which the operation such as described above is rendered enables provision of an endoscope apparatus 1 that can drive one image pickup device mounted in an endoscope 3 in the first drive mode that can provide a high frame rate and generate a smooth movie that is highly responsive to a moving object, and in the second drive mode that can increase an S/N ratio to obtain a high-quality image. Accordingly, the present embodiment enables provision of a convenient endoscope apparatus to a user.

Note that although the above description has been provided on the assumption that in the second drive mode, a movie with a frame rate that is lower than that in the first drive mode is obtained, arrangement may be made so that a still image can be generated in the second drive mode, which is a drive mode with a lower frame rate. For example, as indicated by the dotted line in FIG. 1, it is possible that a selecting unit (or setting unit) 30 for the second drive mode is provided in the main body portion 4, and in response to a selection (or setting) operation by a user, the control circuit 22 performs control to selectively generate either of a movie with a low frame rate and a still image.

If a movie is selected, the control circuit 22 performs control so as to perform the above-described operation. On the other hand, if a still image is selected, the control circuit 22 performs control so as to, in the control operation where a movie is selected, make the frame buffer controller 24 bring a frame buffer in which an image signal for one frame has been written after the switching of the mode, into a writing-prohibited state, to repeatedly read a same image from the frame buffer brought into the writing-prohibited state.

Thus, the monitor 5, which is a display unit, repeatedly displays a same image as a still image. Also, a user can select a still image to observe a high-quality image in a stationary state.

Second Embodiment

Figure 8:
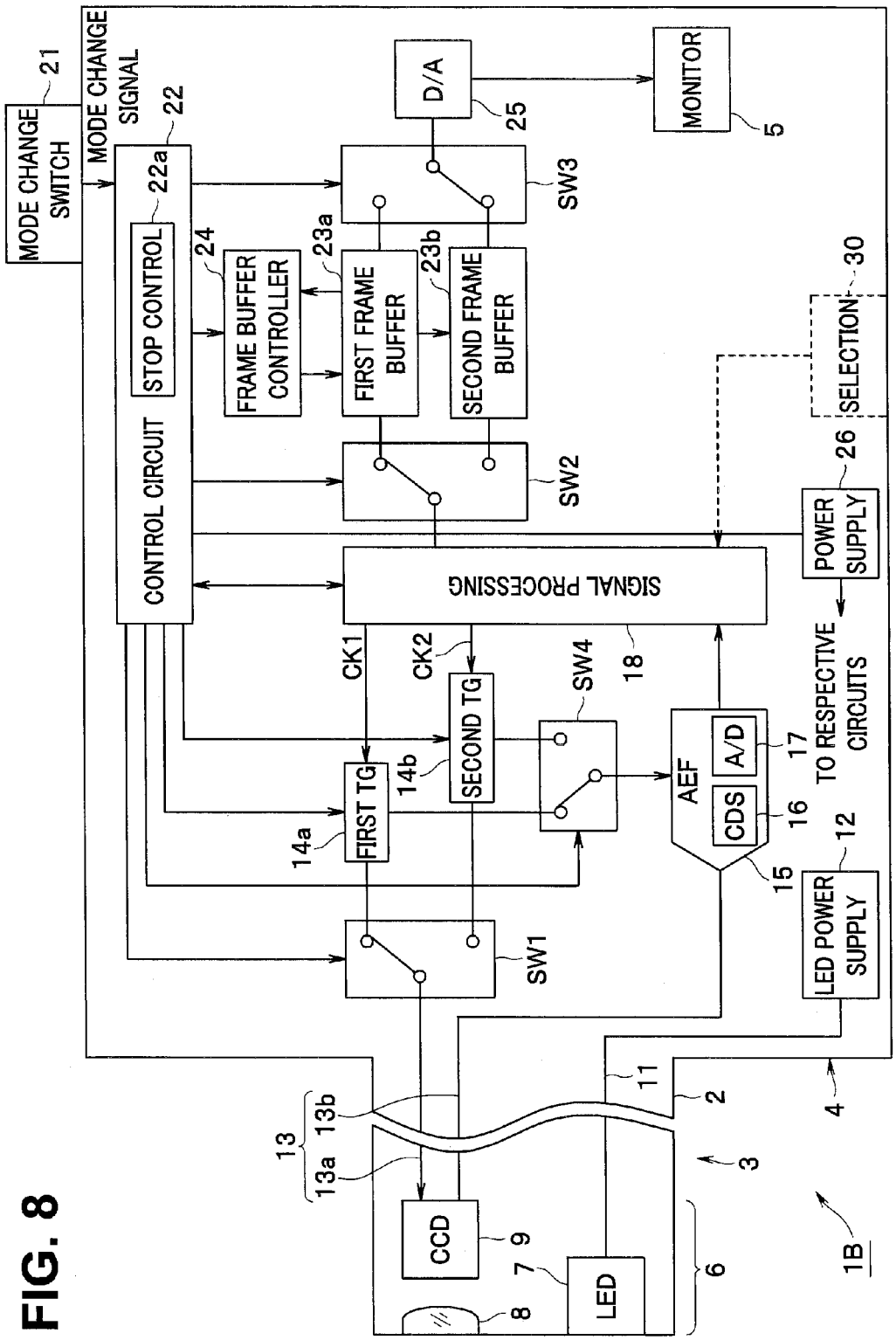
FIG. 8 is a diagram illustrating an overall configuration of an endoscope apparatus according to a second embodiment of the present invention.

Next, a second embodiment of the present invention will be described. FIG. 8 illustrates a configuration of an endoscope apparatus 1B according to a second embodiment of the present invention. Although in the endoscope apparatus 1 according to the first embodiment illustrated in FIG. 1, one TG 14 is used, in an endoscope apparatus 1B, which is illustrated in FIG. 8, two TGs, that is, a first TG 14a and a second TG 14b are provided.

In the first embodiment, as a result of first horizontal transfer clocks CK1 and second horizontal transfer clocks CK2 being selectively inputted (or inputted with the one switched to the other) to one TG 14, the TG 14 selectively generates CCD drive signals for the first drive mode and CCD drive signals for the second drive mode.

On the other hand, in the present embodiment, the first TG 14a generates only CCD drive signals for a first drive mode, and the second TG 14b generates only CCD drive signals for a second drive mode. In other words, first horizontal transfer clocks CK1 are inputted to the first TG 14a, and the first TG 14a generates only CCD drive signals for the first drive mode. Also, second horizontal transfer clocks CK2 are inputted to the second TG 14b, and the second TG 14b generates only CCD drive signals for the second drive mode.

Also, a first switch SW1 corresponding to the first switch SW1 arranged between the signal processing circuit 18 and the TG 14 in FIG. 1 is arranged on the output side of the TG 14, to select CCD drive signals of the first TG 14a or CCD drive signals of the second TG 14b and output the selected CCD drive signals to a CCD 9.

Switching of the first switch SW1 is controlled by a SW1 switching signal from a control circuit 22. For example, when the SW1 switching signal is at an L level (see FIG. 9), the first switch SW1 selects the first TG 14a and outputs an output of the first TG 14a to the CCD 9.

On the other hand, when the SW1 switching signal is at an H level (see FIG. 9), the first switch SW1 selects the second TG 14b, and an output of the second TG 14b is outputted to the CCD 9.

As described above, the signal processing circuit 18 outputs first horizontal transfer clocks CK1 to the first TG 14a, and outputs second horizontal transfer clocks CK2 to the second TG 14b.

Also, AFE pulses generated by the first TG 14a and AFE pulses generated by the second TG 14b are applied to an AFE 15 via a fourth switch SW4. The control circuit 22 controls switching of the fourth switch SW4 in synchronization with the first switch SW1.

Note that when the first drive mode is set, the control circuit 22 performs control to provide switching states of the switches SW1 to SW4 such as illustrated in FIG. 8.

Also, the control circuit 22 has a function of a stop control circuit 22a that controls whether power supply to the first TG 14a and the second TG 14b from the power supply circuit 26 is turned on or off. More specifically, in the case of operation in the first drive mode, the control circuit 22 turns off the power supply to the second TG 14b from the power supply circuit 26. Note that the stop control circuit 22a may be provided outside the control circuit 22.

Also, in the operation state in the first drive mode, upon a mode change instruction being provided, the control circuit 22 turns the off state of the power supply to the second TG 14b from the power supply circuit 26 to an on state at a timing of the provision of the mode change instruction.

Furthermore, when the operation enters a state in which the CCD 9 is driven by the second TG 14b in the second drive mode, the control circuit 22 turns the on state of the power supply to the first TG 14a from the power supply circuit 26 to an off state.

The rest of configuration is similar to that of the first embodiment illustrated in FIG. 1.

The endoscope apparatus 1B according to the present embodiment includes: the CCD 9, which is an image pickup device including an effective pixel region 31a to be used for display and an ineffective pixel region 31b not to be used for display, in order to pick up an image of an object; a signal cable 13, which is a signal transmission cable disposed in an insertion portion 2, the signal cable 13 transmitting an output signal of the image pickup device; one analog front-end circuit 15 that receives an input of the output signal of the image pickup device transmitted via the signal transmission cable, and samples the output signal and converts a resulting output signal into a digital signal; a signal processing circuit 18 that performs signal processing on the output signal of the image pickup device inputted via the analog front-end circuit 15; first and second timing generators 14a and 14b that generate first and second image pickup drive signals for selectively driving the image pickup device in the first and second image pickup device drive modes for driving the image pickup device using first and second horizontal transfer clocks having different frequencies, respectively; and the control circuit 22 that controls operation of the first and second timing generators 14a and 14b and operation of the signal processing circuit 18, and when the first image pickup device drive mode is switched to the second image pickup device drive mode, the control circuit 22 performs control so that a change is made to the frequency of the second horizontal transfer clock for the second timing generator 14b to generate the second image pickup drive signal during a period from a start of transfer of pixel information in the ineffective pixel region 31b of the image pickup device after completion of transfer of pixel information in the effective pixel region 31a of the image pickup device until before an output of a next vertical synchronization signal by the first timing generator 14a, and then output the first vertical synchronization signal of the next frame.

Figure 9:
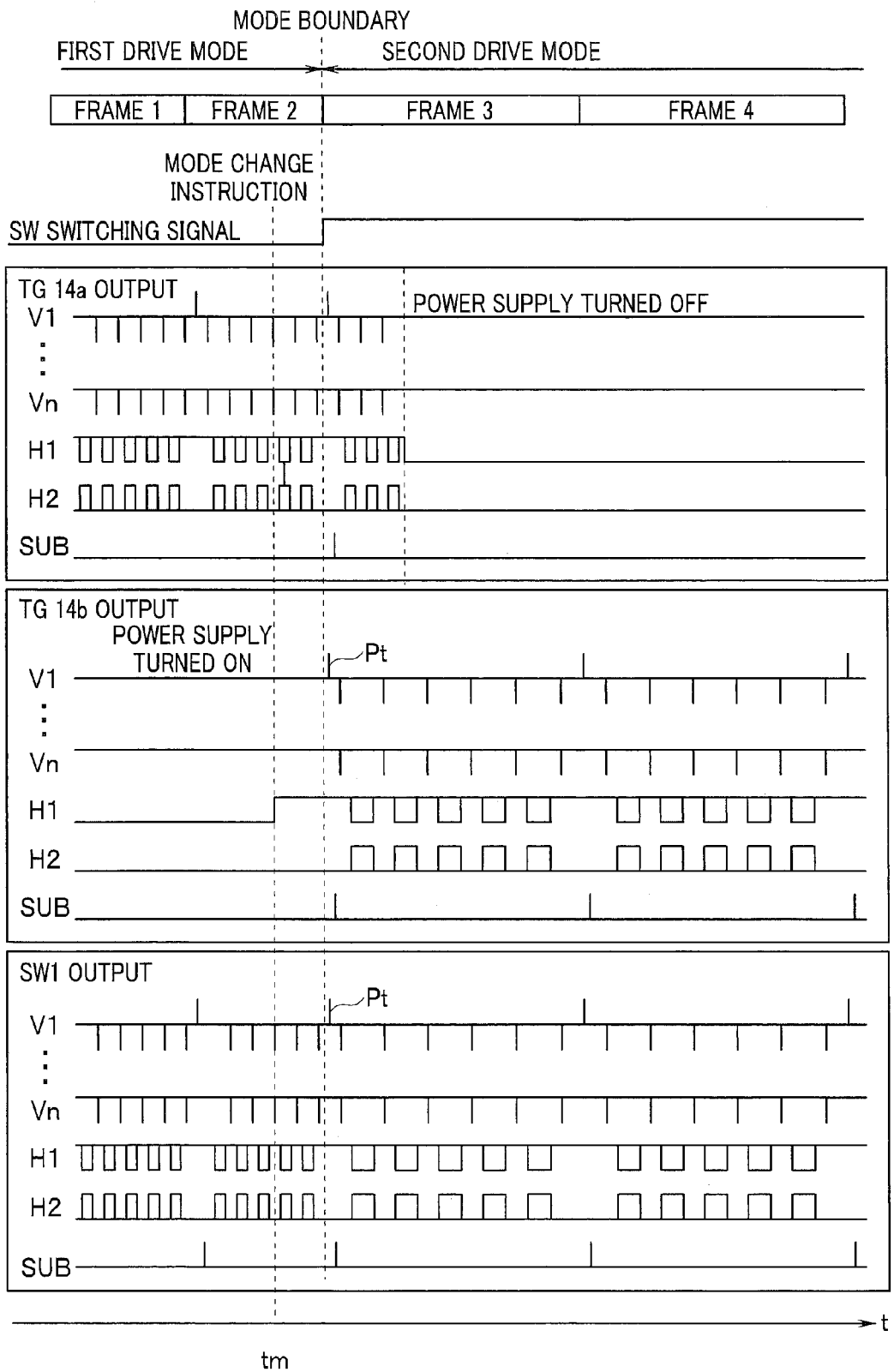
FIG. 9 is a timing chart illustrating operation when a mode change instruction is provided in the second embodiment.

Next, operation of the present embodiment will be described with reference to the timing chart in FIG. 9 and the flowchart in FIG. 10.

As in step S1 in the first embodiment, in first step S21, a user performs an operation to provide an instruction for setting the first drive mode.

According to the operation for the instruction in step S21, in next step S22, as illustrated in FIG. 8, the control circuit 22 switches the first switch SW1 and the fourth switch SW4 to the first TG 14a side. Also, in step S23, as illustrated in FIG. 8, the control circuit 22 makes settings for switching each of the second switch SW2 and the third switch SW3 to the writing-side frame buffer and the readout-side frame buffer. Note that the switching of the second switch SW2 and the third switch SW3 is alternately performed in cycles of one frame.

Then, as indicated in step S24, the first TG 14a drives the CCD 9 in the first drive mode. An output signal of the CCD driven in the first drive mode is subjected to signal processing by the signal processing circuit 18 and outputted to a monitor 5. As indicated in step S25, the monitor 5 displays an image generated by the signal processing circuit 18, which results from the driving in the first drive mode. As indicated in step S26, the control circuit 22 monitors whether or not an operation to provide a mode change instruction is performed, and if no operation to provide a mode change instruction is performed, the operation returns to the processing in step S23. The left side of FIG. 9 indicates a timing chart for CCD drive signals from the first TG 14a. Note that in this state, the second TG 14b is in an off state.

In step S26, upon the control circuit 22 detecting a mode change signal resulting from the operation to provide the mode change instruction, as indicated in step S27, the control circuit 22 turns on the power supply to the second TG 14b. In FIG. 9, tm denotes a time when an operation to provide a mode change instruction was performed, and indicates that the power supply to the second TG 14b is turned from the off state to an on state.

Furthermore, as indicated in step S28, the control circuit 22 waits for completion of startup of the second TG 14b. Then, after startup of the second TG 14b, as indicated in step S29, the control circuit 22 waits until a timing of generation of a next vertical synchronization signal is close.

When the control circuit 22 waits for the next vertical synchronization signal, as indicated in step S30, the control circuit 22 determines whether or not readout of the effective pixel region 31a has ended (has been completed), and waits until an end (completion) of readout of the effective pixel region 31a.

If it is determined that the readout of the effective pixel region 31a has ended (has been completed), in step S31, the control circuit 22 switches each of the first switch SW1 and the fourth switch SW4 to the second TG 14b side, and then, in step S32, the second TG 14b generates the next vertical synchronization signal. From here, operation in the second drive mode starts. In step S33, the control circuit 22 performs control to switch the second switch SW2 to the writing-side frame buffer.

Also, in step S34, the control circuit 22 turns an on state of the power supply to the first TG 14a to an off state in response to the operation in the second drive mode. As illustrated in the diagram on the right side of the mode boundary in FIG. 9, the power supply to the first TG 14a is turned off, which brings the first TG 14a into a state in which the first TG 14a generates no CCD drive signals.

Also, as indicated in step S35, the control circuit 22 waits for a one-frame period from a time of the start of the second drive mode.

Then, after passage of the one-frame period, as indicated in step S36, the control circuit 22 switches the third switch SW3 from a state before the switching. Then, from a frame buffer in which an image read out from the CCD 9 in the second drive mode has been written, the image is read out and outputted to the monitor 5.

As indicated in step S37, the image read out from the CCD 9 in the second drive mode is displayed on the monitor 5. Then, the mode change processing illustrated in FIG. 10 ends. As described in the first embodiment, upon a user performing an operation to provide a mode change instruction in the second drive mode, the second drive mode is switched again to the first drive mode.

According to the present embodiment, effects similar to those of the first embodiment are provided, and since the first TG 14a and the second TG 14b solely generate CCD drive signals for the first drive mode and CCD drive signals for the second drive mode, respectively, in a mode change, CCD drive signals actually subjected to the mode change can be generated in a shorter period of time compared to a case where both CCD drive signals are generated by switching of one TG 14.

Thus, an image in a drive mode according to a mode change instruction can be generated in a short waiting time period from provision of the instruction, and the generated image can be displayed on the monitor 5. Thus, the user friendliness can be enhanced.

Furthermore, during periods in which the first TG 14a and the second TG 14b are not actually used, the first TG 14a and the second TG 14b are turned off, respectively, enabling power saving.

Third Embodiment

Figure 11:
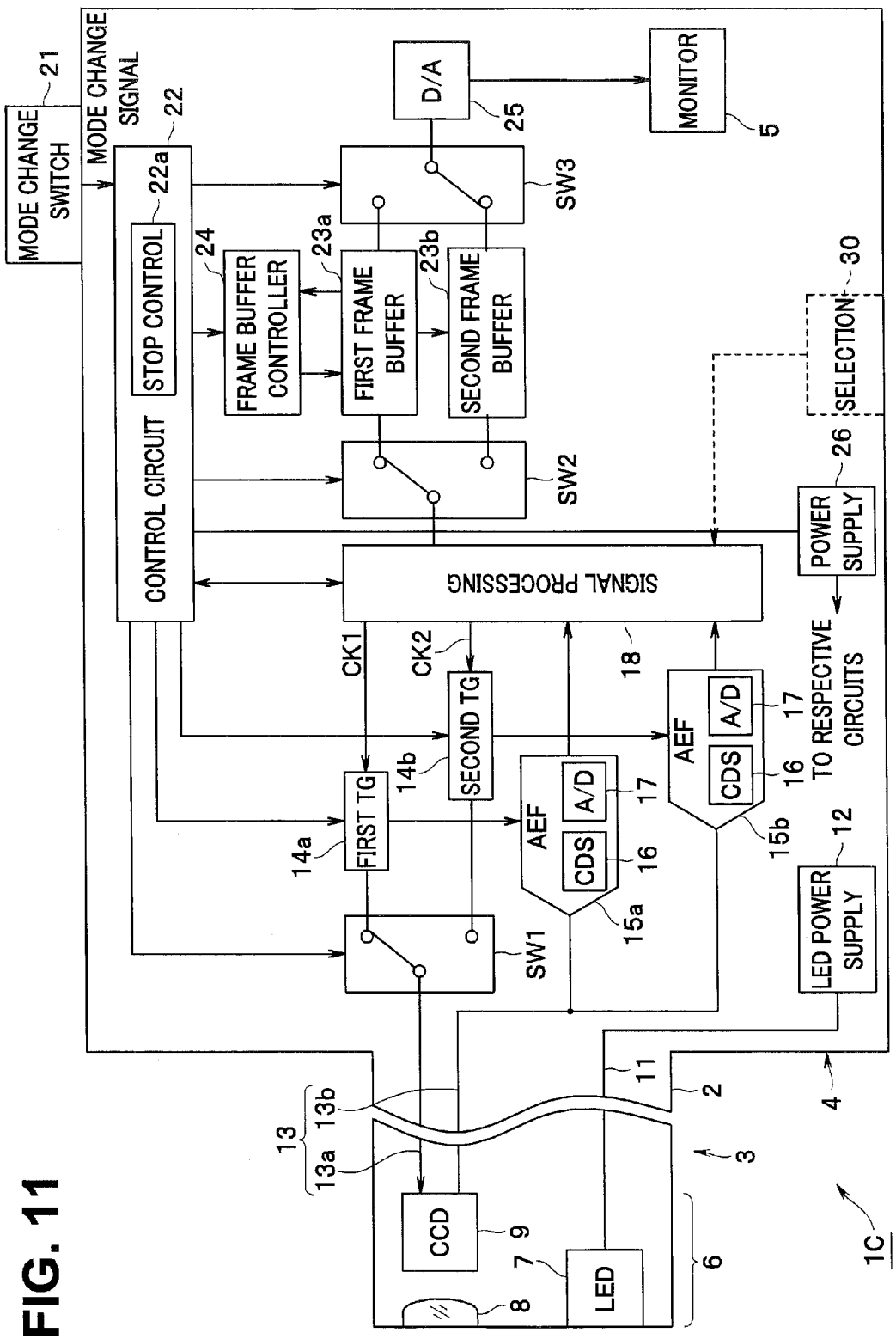
FIG. 11 is a diagram illustrating an overall configuration of an endoscope apparatus according to a third embodiment of the present invention.

Next, a third embodiment of the present invention will be described. FIG. 11 illustrates a configuration of an endoscope apparatus 1C according to a third embodiment of the present invention. The endoscope apparatus 1C according to the present embodiment corresponds to a modification of the endoscope apparatus 1B according to the second embodiment.

The endoscope apparatus 1C according to the present embodiment has a configuration in which a first AFE 15a and a second AFE 15b are provided instead of one AFE 15 and the fourth switch SW4 is not provided in the endoscope apparatus 1B illustrated in FIG. 8. Then, the first TG 14a applies AFE pulses generated using first horizontal transfer clocks CK1 to the first AFE 15a, and the second TG 14b applies AFE pulses generated using second horizontal transfer clocks CK2 to the second AFE 15b.

Note that each of the first AFE 15a and the second AFE 15b sample an output signal of the CCD 9 via a CDS circuit 16, amplifies the output signal of the CDS circuit 16 via an AGC circuit, which is a gain-variable amplifier that performs amplification with a variable gain according to a signal level, and subjects the analog output signal amplified by the AGC circuit to A/D conversion via an A/D conversion circuit 17 and outputs the resulting signal to the signal processing circuit 18. The rest of configuration is similar to that illustrated in FIG. 8.

The endoscope apparatus 1C according to the present embodiment includes: the CCD 9, which is an image pickup device including an effective pixel region 31a to be used for display and an ineffective pixel region 31b not to be used for display, in order to pick up an image of an object; a signal cable 13, which is a signal transmission cable disposed in an insertion portion 2, the signal transmission cable transmitting an output signal of the image pickup device; first and second analog front-end circuits 15a and 15b that receive an input of the output signal of the image pickup device transmitted via the signal transmission cable, and samples the output signal and converts a resulting output signal into a digital signal; the signal processing circuit 18 that performs signal processing on the output signal of the image pickup device inputted via the analog front-end circuit 15a or 15b; first and second timing generator 14a and 14b that generate first and second image pickup drive signal for selectively driving image pickup device in the first and second image pickup device drive modes for driving the image pickup device using first and second horizontal transfer clocks having different frequencies, respectively, and output sampling pulses to the first and second analog front-end circuits 15a and 15b, respectively; and a control circuit 22 that controls operation of the first and second timing generators 14a and 14b and the signal processing circuit 18, and when the first image pickup device drive mode is switched to the second image pickup device drive mode, the control circuit 22 performs control so that a change is made to the frequency of the second horizontal transfer clock to input the output signal of the second analog front-end circuit 15b to the signal processing circuit 18 and for the second timing generator 14b to generate the second image pickup drive signal during a period from a start of transfer of pixel information in the ineffective pixel region 31b of the image pickup device after completion of transfer of pixel information in the effective pixel region 31a of the image pickup device by the first timing generator 14a until before an output of a next vertical synchronization signal by the first timing generator 14a, and then output the next vertical synchronization signal.

Figure 12:
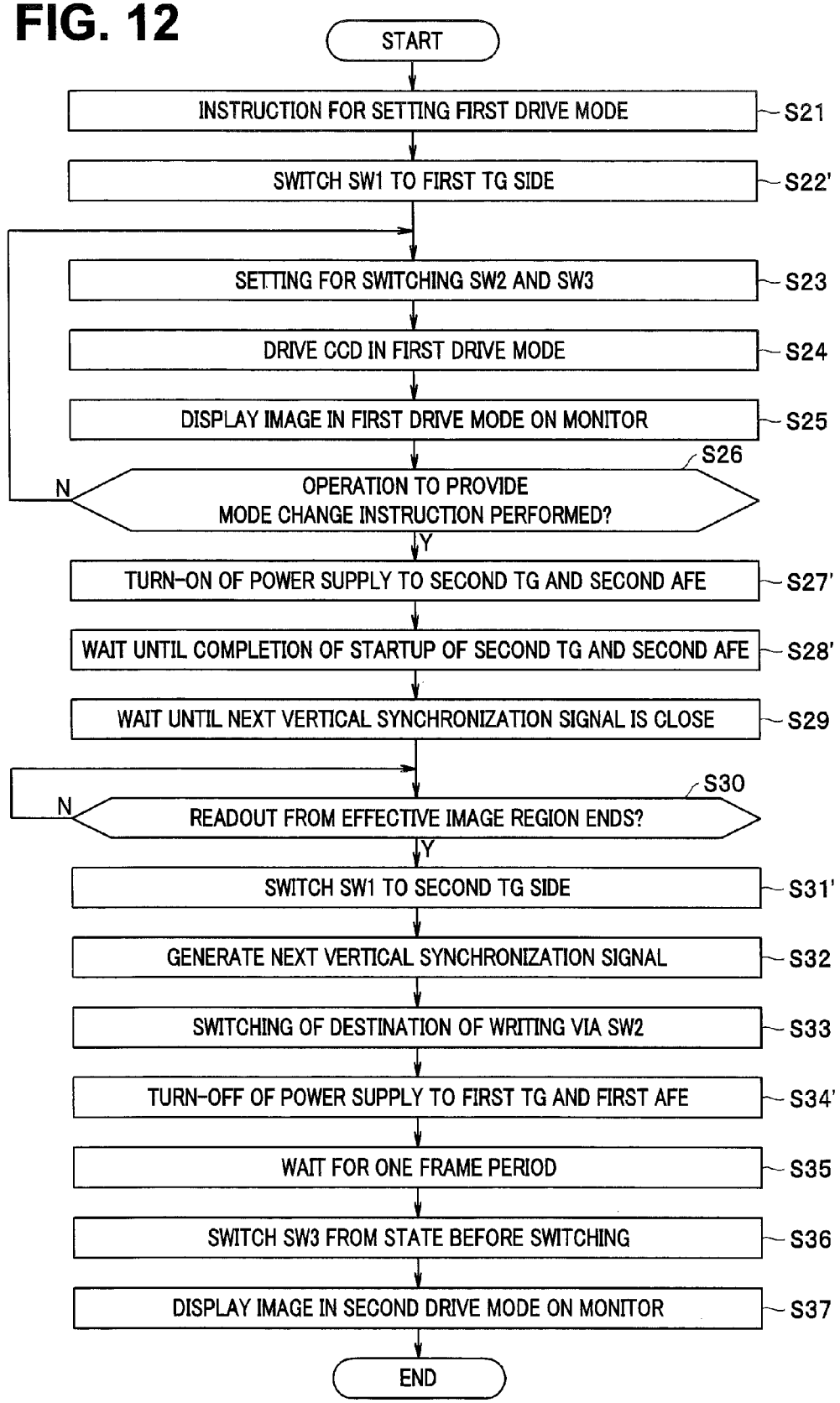
FIG. 12 is a flowchart illustrating typical processing when a mode change instruction is provided in the third embodiment.

Next, operation of the present embodiment will be described with reference to FIG. 12. In the present embodiment, the first AFE 15a operates together with the first TG 14a and the second AFE 15b operates together with the second TG 14b, eliminating the need for switching via the fourth switch SW4 in the second embodiment. Thus, although in the second embodiment, when the first TG 14a or the second TG 14b is not substantially used, the control circuit 22 turns off the power supply to the first TG 14a or the second TG 14b, in the present embodiment, when the first AFE 15a or the second AFE 15b is not substantially used, the control circuit 22 also turns off power supply to the first AFE 15a or the second AFE 15b.

Figure 10:
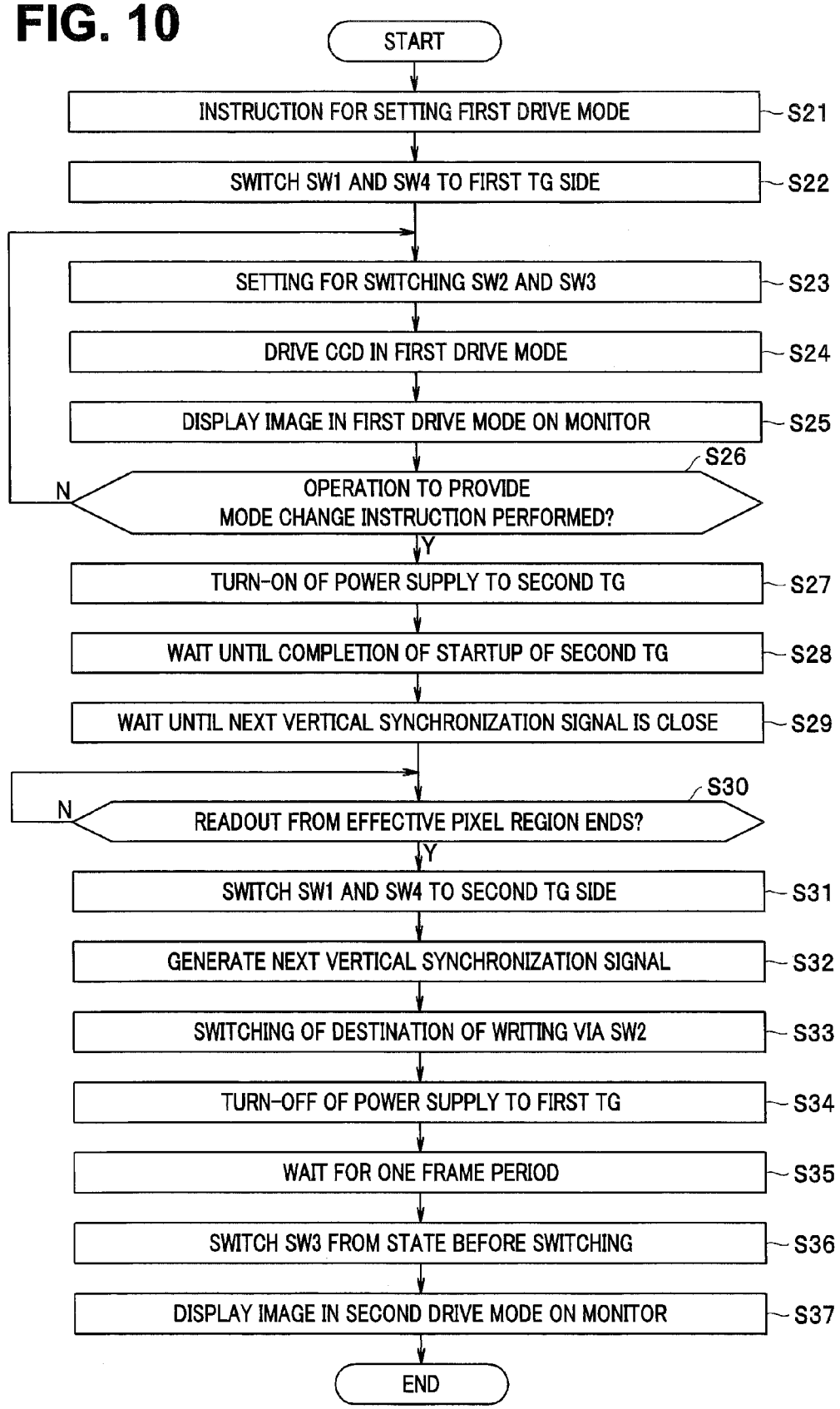
FIG. 10 is a flowchart illustrating typical processing when a mode change instruction is provided in the second embodiment.

Thus, a description will be provided only on parts that are different from those in FIG. 10. As in the case in FIG. 10, processing in first step S21 is performed, and in next step S22', the control circuit 22 switches only the first switch SW1 to the first TG 14a side.

Note that in this state, the control circuit 22 performs control so that the first AFE is on and the second AFE 15b is off. In following steps S23 to step S26, the operation is similar to that in FIG. 10. In step S26, if an operation to provide a mode change instruction is performed, in next step S27', the control circuit 22 turns on the power supply to the second AFE 15b together with the second TG 14b. Also, in next step S28', the control circuit 22 waits until completion of startup of the second TG 14b and the second AFE 15b.

In following steps S29 and S30, the operation is similar to that in FIG. 10. In step S31' following step S30, the control circuit 22 switches the first switch SW1 to the second TG 14b side. In following steps S32 and S33, the operation is similar to that in FIG. 10. In step S34' following step S33, the control circuit 22 turns off the power supply to the first AFE 15a together with the first TG 14a. In subsequent steps S35 to S37, the operation is similar to that in FIG. 10.

According to the present embodiment, effects that are similar to those of the second embodiment are provided, and a waiting time period from switching between the first AFE 15a and the second AFE 15b via the fourth switch SW4 in second embodiment until the first AFE 15a or the second AFE 15b actually enters an operating state can be reduced. In other words, in the present embodiment, the first AFE 15a or the second AFE 15b operates in conjunction with the first TG 14a or second TG 14b, respectively, in order to eliminate the need for switching, which enables elimination of a wait time period for switching.

Fourth Embodiment

Figure 13:
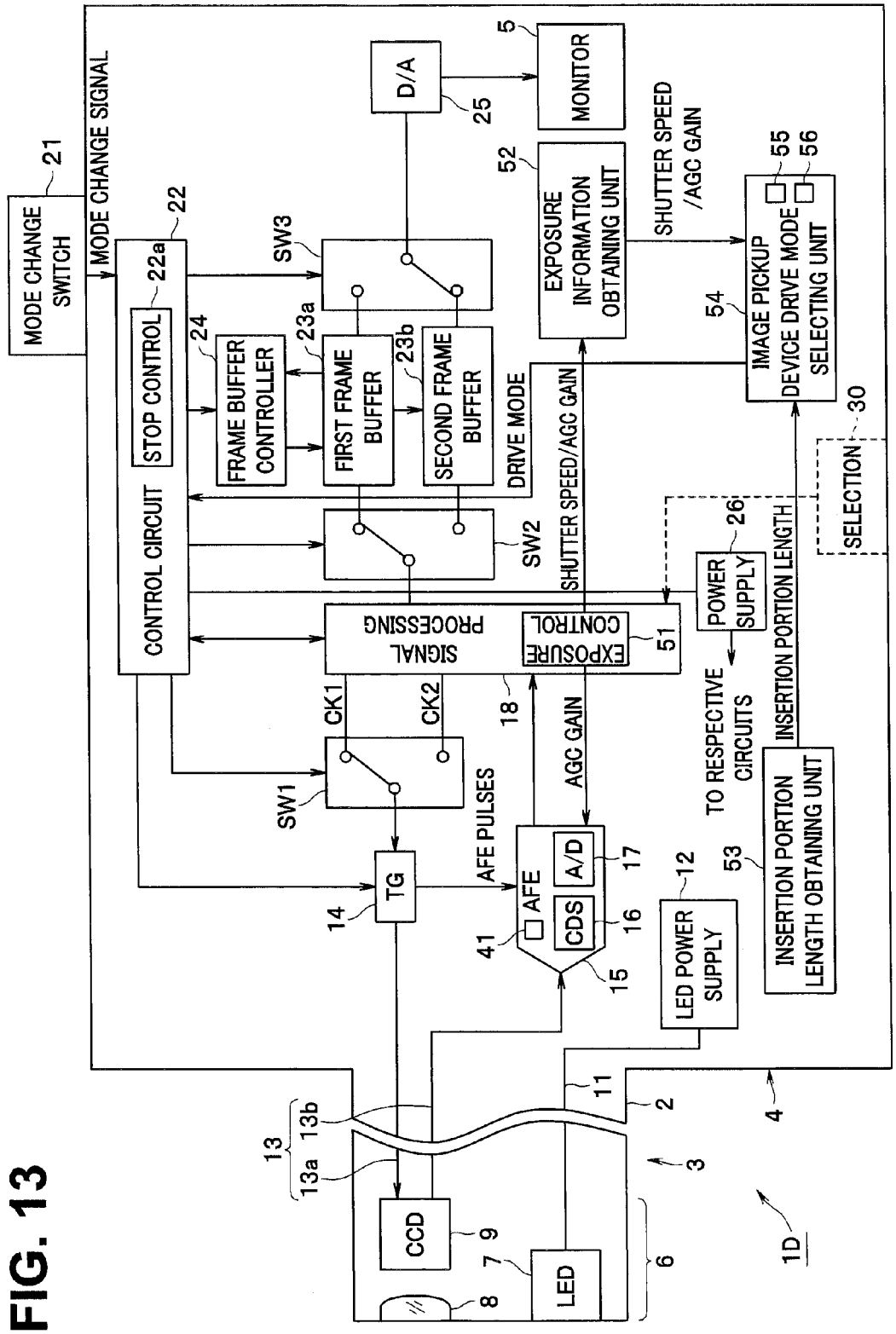
FIG. 13 is a diagram illustrating an overall configuration of an endoscope apparatus according to a fourth embodiment of the present invention.

Next, a fourth embodiment of the present invention will be described. FIG. 13 illustrates a configuration of an endoscope apparatus 1D according to a fourth embodiment of the present invention. The endoscope apparatus 1D according to the present embodiment corresponds to, for example, an modification of the endoscope apparatus 1 according to the first embodiment, and further includes an exposure control unit 51, an exposure information obtaining unit 52, an insertion portion length obtaining unit 53 and an image pickup device drive mode selecting unit 54. Here, description of components that are the same as those of the first embodiment will be omitted, and only parts that are different from those of the first embodiment will be described. The same applies to fifth and sixth embodiments, which will be described later.

The endoscope apparatus 1D according to the present embodiment has a configuration in which the signal processing circuit 18 includes the exposure control unit (or exposure control circuit) 51, which is exposure control means for performing control to provide a proper exposure amount using information on an image picked up using the CCD 9, in the endoscope apparatus 1 illustrated in FIG. 1. The exposure control unit 51 controls a shutter speed for determining a period in which the CCD 9 actually picks up an image (receives light) and a value of an AGC gain of an AGC circuit in an AFE 15 (41 in FIG. 13) to provide a proper exposure amount.

Also, in the main body portion 4, the exposure information obtaining unit 52, which is exposure information obtaining means for obtaining the shutter speed and the AGC gain information provided by the exposure control unit 51 in the signal processing circuit 18, as exposure information, the insertion portion length obtaining unit 53, which is insertion portion length obtaining means for obtaining information on an insertion portion length, which is a length of an insertion portion 2, and the image pickup device drive mode selecting unit 54, which is image pickup device drive mode selection means for selectively determining an image pickup device drive mode based on the exposure information and the insertion portion length information are provided.

As described above, the exposure control unit 51 performs control to provide a proper exposure amount. More specifically, the exposure control unit 51 increases the shutter speed if an image of an object is bright, and decreases the shutter speed if the image is dark. If an image of an object is still dark in despite of the shutter speed being set to be lowest, the exposure control unit 51 increases the AGC gain.

The insertion portion length obtaining unit 53 obtains information on a length of an insertion portion of each endoscope 3. In the case of an endoscope apparatus in which an endoscope 3 including an insertion portion 2 and a main body portion 4 are integrated, insertion portion length information is stored in, for example, a ROM in the main body portion 4.

In the case of a structure in which an endoscope 3 including an insertion portion 2 and a main body portion 4 are detachably connected, the insertion portion length obtaining unit 53 obtains a length of the insertion portion of the endoscope 3 connected to the main body portion 4, from information in a ROM that stores unique information, which is provided on the endoscope 3 side.

Shutter speed and AGC gain information, which is exposure information obtained by the exposure information obtaining unit 52, and insertion portion length information obtained by the insertion portion length obtaining unit 53 are inputted to the image pickup device drive mode selecting unit 54. As illustrated in FIG. 14, the image pickup device drive mode selecting unit 54 includes information storing means that stores, in advance, a determination table (or a selection table) 55 in which exposure information and insertion portion length information and information for selectively determining a proper drive mode from the exposure information and the insertion portion length information are associated with each other.

Using the table information in the determination table 55, the image pickup device drive mode selecting unit 54 selects a drive mode that meets relevant conditions from a first drive mode and a second drive mode, based on the shutter speed and AGC gain information, which is exposure information inputted, and the insertion portion length information. In the determination table 55, each drive mode (proper drive mode) that is more desirable in the first drive mode and the second drive mode is found out in advance according the two types of information and stored in advance.

The image pickup device drive mode selecting unit 54 automatically selects a proper drive mode from the first drive mode and the second drive mode using the table information in the determination table 55, and sends information on the selected drive mode to the control circuit 22.

The control circuit 22 performs control so as to drive the CCD 9, which is an image pickup device, in the drive mode sent from the image pickup device drive mode selecting unit 54. In other words, the control circuit 22 sets the drive mode selected by the device drive mode selecting unit 54 (from the two drive modes for driving the image pickup device) to drive the image pickup device in that drive mode.

Since a signal cable 13 is inserted in the insertion portion 2 in a longitudinal direction thereof, if the insertion portion length is long, the signal amplitude is small compared to a case where the insertion portion length is short even under same exposure conditions, resulting in an increase in exogenous noise. Conversely, if the insertion portion length is short, an environment in which driving in the first drive mode that provides a high drive frequency can easily be performed is provided.

In the determination table 55, information having a tendency of basically selecting the first drive mode that provides a high drive frequency if the insertion portion length is short, and selecting the second drive mode that provides a low drive frequency if the insertion portion length is long and the object is dark is stored.

The image pickup device drive mode selecting unit 54 obtains a proper drive mode using the table information in the determination table 55 and sends the proper drive mode to the control circuit 22. The control circuit 22 controls the TG 14 so as to drive the CCD 9, which is an image pickup device, in the drive mode selected by the image pickup device drive mode selecting unit 54. Then, the TG 14 drives the image pickup device in the drive mode selected by the image pickup device drive mode selecting unit 54, by means of the control performed by the control circuit 22.

For example, when the first drive mode is set, if the insertion portion length exceeds 5000 mm, which makes it impossible to obtain sufficient brightness by means of exposure control (i.e., if an AGC gain exceeding 10 dB is needed), the image pickup device drive mode selecting unit 54 sends drive mode information for a change to select the second drive mode to the control circuit 22. The control circuit 22 performs control so that the first drive mode is switched to the second drive mode to drive the CCD 9. In this case, the signal attenuation can be reduced and a high-quality image with a good S/N ratio can be displayed on a monitor 5.

Also, in the case of an endoscope apparatus whose insertion portion 2 is short, the effect of signal attenuation attributable to the cable length is small, and thus, a smooth object can be displayed at a high frame rate on the monitor 5 by setting the first drive mode. Also, if the insertion portion length is long, the signal attenuation effect is large, and in the case of, in particular, a dark object, if a high gain is set, a high-quality image with the signal attenuation effect reduced to be low can be displayed on the monitor 5 by setting the second drive mode.

Note that, in the image pickup device drive mode selecting unit 54, a delay amount data storing unit 56, which is storing means for storing AFE pulse timing delay amount data (abbreviated as "delay amount data"), which is information for adjusting timings for AFE pulses to be outputted from the TG 14 to the CDS circuit 16 in the AFE 15 according to an insertion portion length or an image pickup device drive mode, may be provided.

From transmission of an output signal of the CCD 9 via (a signal wire 13*b* in) a signal cable 13 until an actual input of the output signal to the AFE 15, a delay corresponding to an insertion length (length of the signal wire 13b in the signal cable 13) occurs. Therefore, a relationship between each insertion length and a delay time period occurring for the insertion length is found out in advance and delay amount data relating the both to each other is stored for each image pickup device drive mode in a delay amount data storing unit 56.

The image pickup device drive mode selecting unit 54 sends delay amount data corresponding to an insertion length obtained by the insertion portion length obtaining unit 53 to the control circuit 22.

The control circuit 22 sends the received delay amount data to the TG 14, and the TG 14 generates AFE pulses (including sampling pulses) delayed by the amount of the delay amount data and outputs the AFE pulses to (the CDS circuit 16 in) the AFE 15. Then, the CDS circuit 16 extracts signal components based on the delayed sampling pulses at a timing when the output signal of the CCD 9 is inputted with delay.

Note that in reality, drive signals for the TG 14 to drive the CCD 9 also drive the CCD 9 with a delay time period corresponding to the length of the signal wire 13a, and thus the control circuit 22 performs control to send delay amount data with this delay time period taken into account, to the TG 14.

Such configuration as above enables the CDS circuit 16 to sample signal components of the output signal of the CCD 9 with good accuracy at timings when the signal components are actually inputted even in a case where the insertion length is long (large), and thus to extract a signal with good quality. In addition to that, the configuration provides operations and effects that are similar to those of the first embodiment.

Note that although the present embodiment has been described in terms of a case where the exposure control unit 51, etc., are provided to the first embodiment, the same can apply to the second embodiment or the third embodiment. Furthermore, the same is applicable also to a fifth embodiment and a sixth embodiment, which will be described below.

Fifth Embodiment

Figure 15:
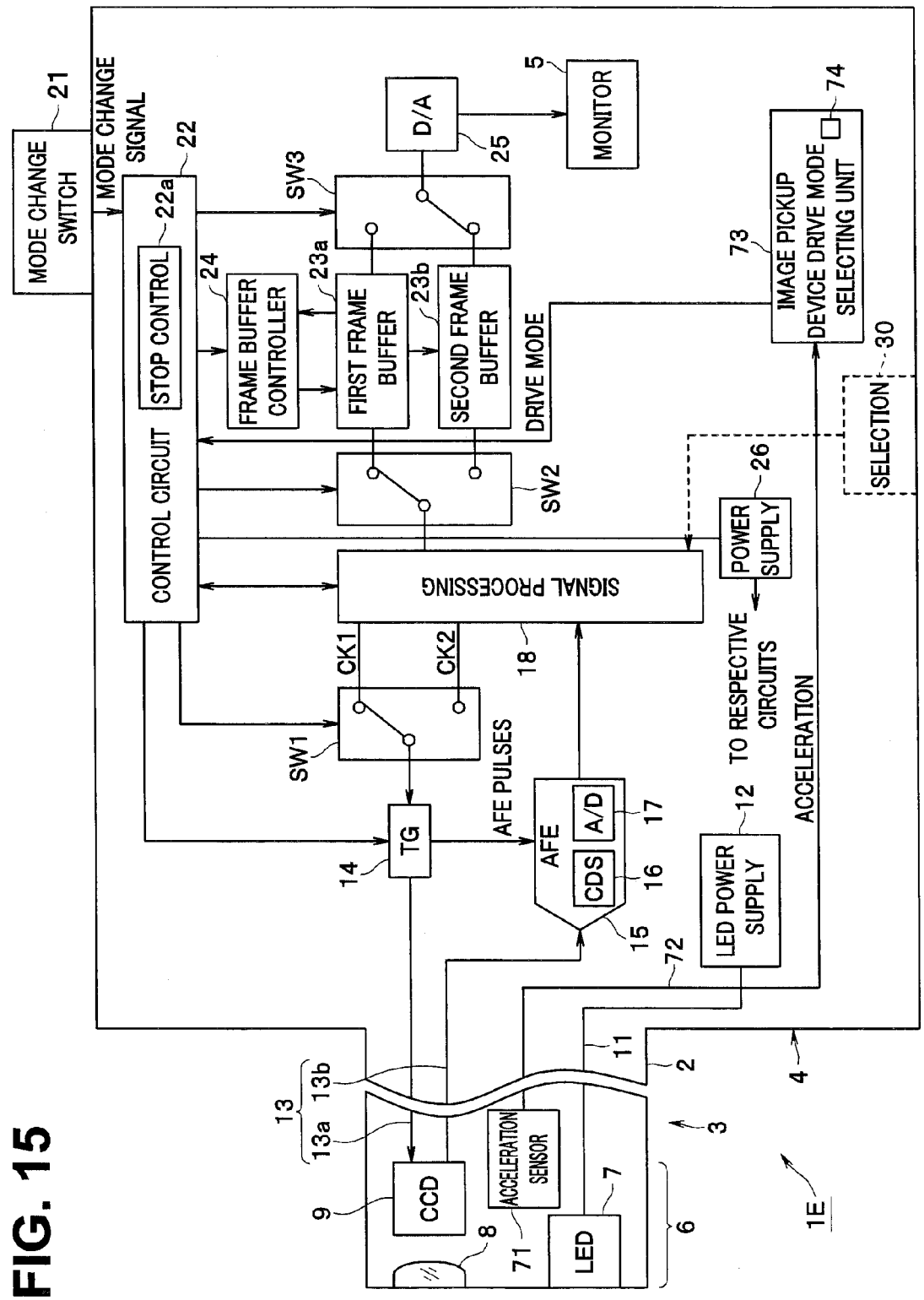
FIG. 15 is a diagram illustrating an overall configuration of an endoscope apparatus according to a fifth embodiment of the present invention.

Next, a fifth embodiment of the present invention will be described. FIG. 15 is illustrates a configuration of an endoscope apparatus 1E according to a fifth embodiment of the present invention. The endoscope apparatus 1E according to the present embodiment corresponds to, for example, a modification of the endoscope apparatus 1 according to the first embodiment, in which an acceleration sensor 71 and an image pickup device drive mode selecting unit 73 are further provided.

The endoscope apparatus 1E according to the present embodiment has a configuration in which as a motion sensor for detecting a motion (more specifically, an acceleration) of a distal end portion 6 of an insertion portion 2 in the distal end portion 6, for example, an acceleration sensor 71 is provided in the endoscope apparatus 1 illustrated in FIG. 1. The acceleration sensor 71 detects an amount of motion of the distal end portion 6 in the form of a three-dimensional acceleration vector, and outputs a signal of the detection to the image pickup device drive mode selecting unit 73, which is image pickup device drive mode selection means provided in a main body portion 4, via a signal wire 72 inserted inside the insertion portion 2.

The image pickup device drive mode selecting unit 73 selects a drive mode based on the signal of detection of the acceleration, which is motion information obtained from the acceleration sensor 71, and sends the selected drive mode to the control circuit 22. The control circuit 22 performs control so that the TG 14 drives the CCD 9, which is an image pickup device, in the drive mode selected by the image pickup device drive mode selecting unit 73. In other words, the control circuit 22 makes settings to drive the image pickup device in the drive mode selected by the image pickup device drive mode selecting unit 73 (from two drive modes for driving the image pickup device).

As illustrated in FIG. 16, the image pickup device drive mode selecting unit 73 includes a determination table (selection table) 74 associating values of accelerations of the distal end portion 6 (that is, distal end portion accelerations) detected by the acceleration sensor 71 with information for selectively determining respective proper drive modes, as information storing means. Note that in FIG. 16, the values of accelerations (distal end portion accelerations) are indicated in absolute value.

The image pickup device drive mode selecting unit 73 monitors an acceleration detected by the acceleration sensor 71 and selects (selectively determines) a drive mode corresponding to a value of the detected acceleration with reference to the determination table 74.

The determination table 74 in FIG. 16 stores, in advance, information for, if an acceleration that is equal to or exceeds a certain value (no less than 0.1 G in a typical example in the table in FIG. 16) with a magnitude of an acceleration vector as a threshold value, selecting a first drive mode that provides a high drive frequency, and, if the acceleration has a value that is less than the certain value, regarding the distal end portion 6 of the endoscope 3 as remaining still and selecting a second drive mode that provides a low drive frequency. Here, G denotes the acceleration of gravity.

With such configuration as above, if an endoscope user is moving the insertion portion 2 to an observation target region the user wishes to observe (that is, the insertion portion 2 is moving), image pickup can be performed so as to obtain a smooth image at a high frame rate, and after the distal end portion 6 has moved to a position at which an image of the observation target region can be picked up, if the endoscope user picks up an image of the observation target region (that is, the observation target region remains still), a high-quality image with signal attenuation suppressed can be picked up and the high-quality image can be displayed on a monitor 5. In addition to that, such configuration provides operations and effects that are similar to those of the first embodiment.

Sixth Embodiment

Figure 17:
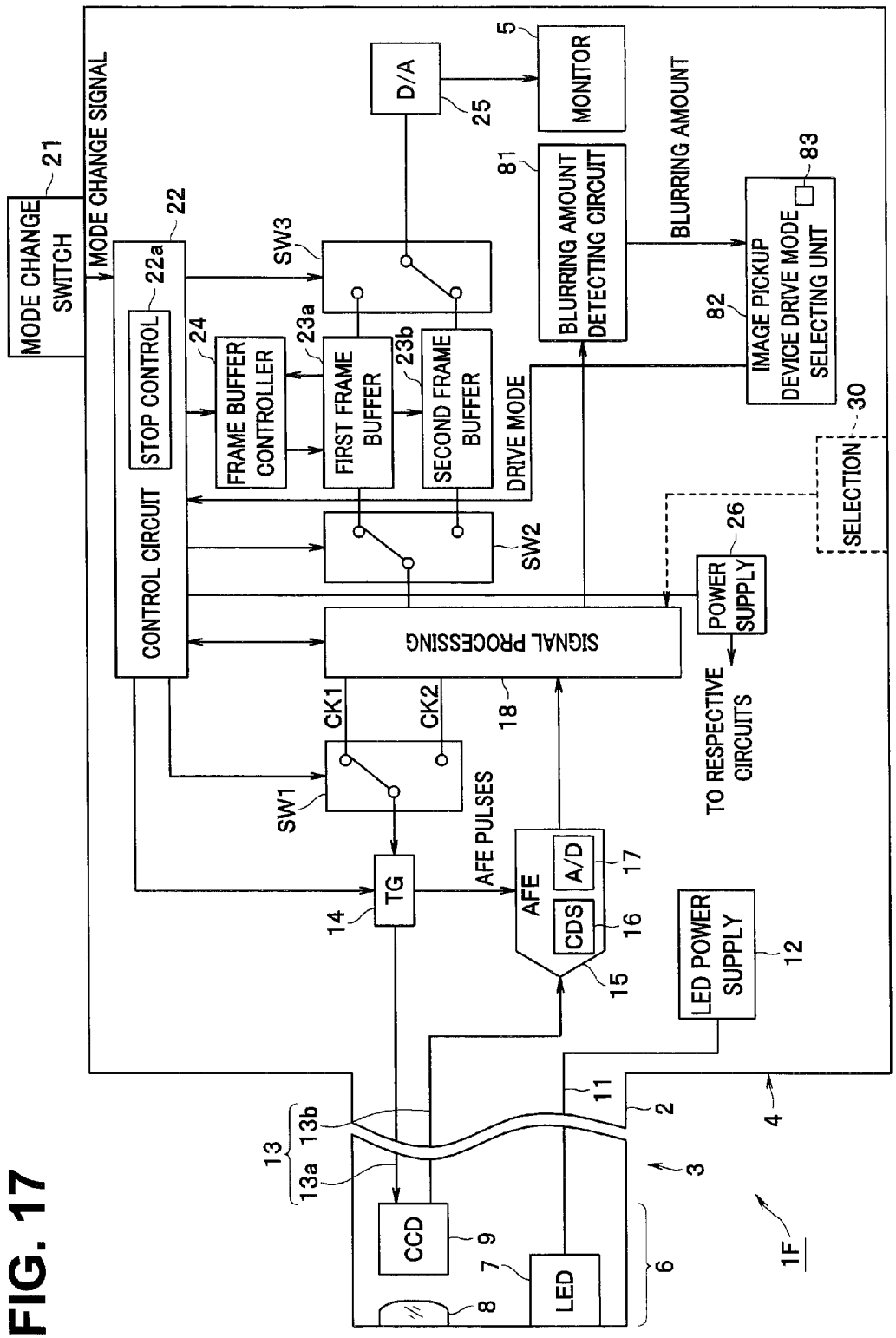
FIG. 17 is a diagram illustrating an overall configuration of an endoscope apparatus according to a sixth embodiment of the present invention.

Next, a sixth embodiment of the present invention will be described. FIG. 17 illustrates a configuration of an endoscope apparatus 1F according to a sixth embodiment of the present invention. The endoscope apparatus 1F according to the present embodiment corresponds to, for example, a modification of the endoscope apparatus 1 according to the first embodiment, and further includes a blurring amount detecting circuit 81 and an image pickup device drive mode selecting unit 82.

The endoscope apparatus 1F according to the present embodiment has a configuration in which a blurring amount detecting circuit 81, which is blurring detecting means for detecting blurring information regarding whether or not an image picked up by the CCD 9 blurs, is provided in, for example, a main body portion 4 in the endoscope apparatus 1 in FIG. 1. Also, in the main body portion 4, an image pickup device drive mode selecting unit 82, which is image pickup device drive mode selection means for selecting (selectively determining) a drive mode based on the blurring amount detected by the blurring amount detecting circuit 81, is provided.

Also, as illustrated in FIG. 18, the image pickup device drive mode selecting unit 82 includes a determination table (selection table) 83 for selecting a drive mode based on a blurring amount, and using the determination table 83, selects a drive mode that is suitable for the relevant case, based on existence or non-existence of blurring detected by the blurring amount detecting circuit 81 or the blurring amount.

Then, the image pickup device drive mode selecting unit 82 sends the selected drive mode to a control circuit 22, and the control circuit 22 performs control so that a TG 14 drives the CCD 9, which is an image pickup device, in the drive mode selected by the image pickup device drive mode selecting unit 82. In other words, the control circuit 22 makes settings so as to drive the image pickup device in the drive mode selected by the image pickup device drive mode selecting unit 82 (from two drive modes for driving the image pickup device).

The blurring amount detecting circuit 81 detects whether or not blurring occurs by comparing a plurality of images (for a plurality of frames) chronologically and sequentially outputted from the signal processing circuit 18 when images of an object are successively picked up by the CCD 9 and determining whether or not an absolute value of an amount of the difference is equal to or exceeds a threshold value. In other words, if the absolute value of the difference amount is less than the threshold value, it is detected (determined) that no blurring occurs, and if the absolute value of the difference amount is equal to or exceeds the threshold value, it is detected (determined) that blurring occurs.

Note that in FIG. 17, the blurring amount detecting circuit 81 may load images in adjacent frames from first frame buffers 23*a* and 23*b* not shown in the drawings and detect whether or not blurring occurs from both images.

When blurring occurs in an image, if driving in a drive mode that enables more reduction of the blurring can be performed, it is favorable to make a drive mode change. Thus, in the present embodiment, the content of the determination table 83 is set so that if blurring occurs, a first drive mode that provides a high drive frequency is selected, and if no blurring occurs, a second drive mode that provides a low drive frequency is selected.

Then, in the present embodiment, arrangement is made so that the image pickup device can be driven in a proper drive mode according to occurrence or non-occurrence of blurring.

With such configuration as above, if a distal end portion 6 of an insertion portion 2 of an endoscope 3 is moving or an object is moving (relative to the distal end portion 6), the first drive mode is selected, enabling image pickup to obtain a smooth image at a high frame rate, and on the other hand, if an object, an image of which is being picked up, and/or the distal end portion 6 of the endoscope 3 remains still, the second drive mode is selected, enabling obtainment of a high-quality image with signal attenuation suppressed. In addition to that, such configuration provides operations and effects that are similar to those of the first embodiment.

Figure 19:
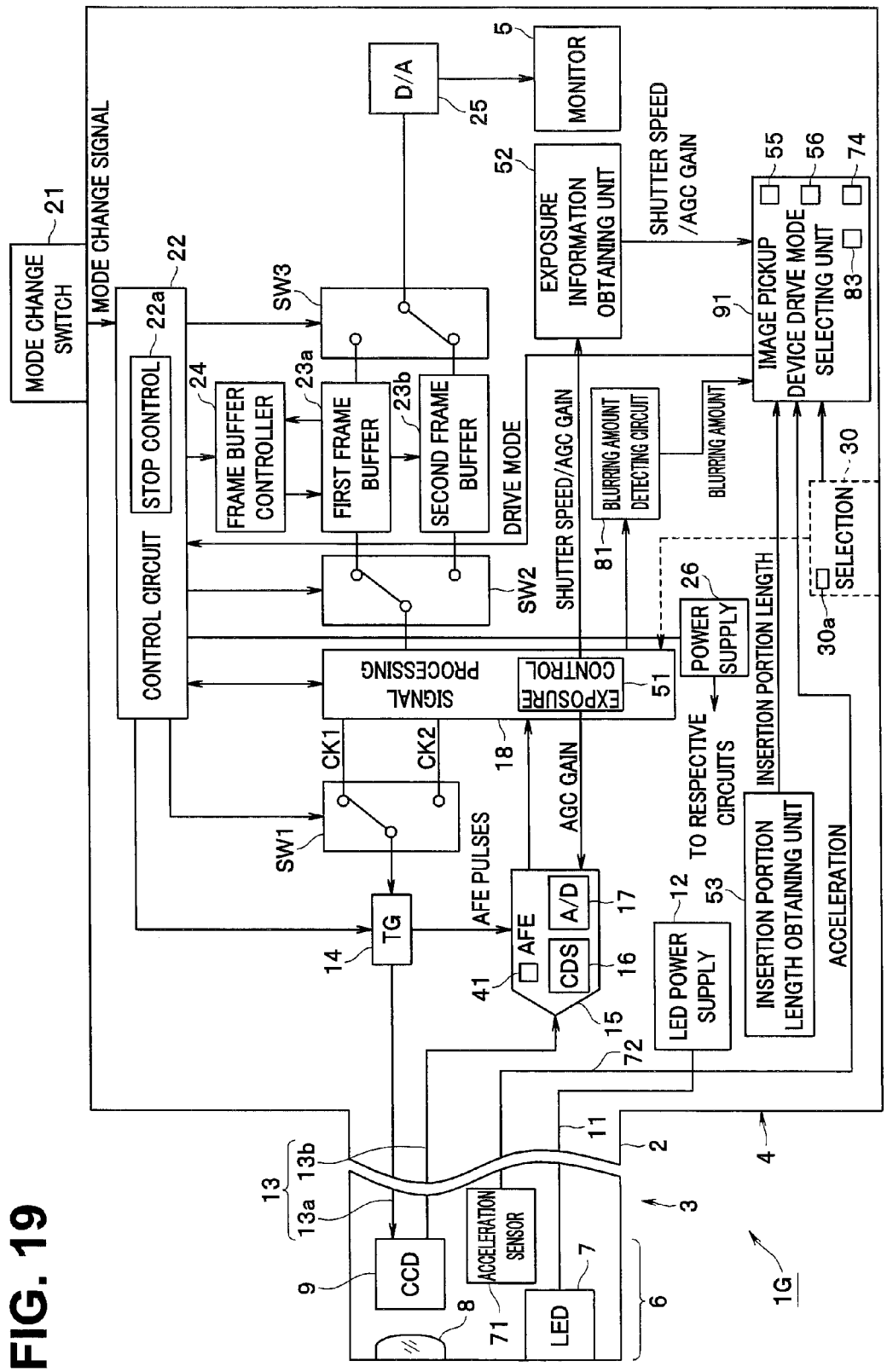
FIG. 19 is a diagram illustrating an overall configuration of an endoscope apparatus according to a modification of a sixth embodiment of the present invention.

Although the above description has been provided with the fourth to sixth embodiments regarded as separate embodiments, arrangement may be made so that a user can select the operation of an arbitrary one of the fourth to sixth embodiments. FIG. 19 illustrates an example of such configuration as a modification of the sixth embodiment.

An endoscope apparatus 1G, which is illustrated in FIG. 19, has a configuration in which respective functions of the exposure control unit 51 and the exposure amount obtaining unit 52 described in the fourth embodiment, the image pickup device drive mode selecting unit 54 (including the determination table 55 and the delay amount data storing unit 56, which are association information storing means), the acceleration sensor 71 described in the fourth embodiment, the image pickup device drive mode selecting unit 73 (including the determination table 74, which is association information storing means), the blurring amount detecting circuit 81 described in the fourth embodiment, and the image pickup device drive mode selecting unit 82 (including the determination table 83, which is association information storing means) are provided in, for example, the endoscope apparatus 1 in FIG. 1.

In FIG. 19, an image pickup device drive mode selecting unit 91 has respective functions of the image pickup device drive mode selecting unit 54 in the fourth embodiment, the image pickup device drive mode selecting unit 73 in the fifth embodiment and the image pickup device drive mode selecting unit 82 in the sixth embodiment. Note that although FIG. 19 illustrates an example configuration in which the determination table 55, the delay amount data storing unit 56, the determination table 74 and the determination table 83 are provided inside the image pickup device drive mode selecting unit 91, the determination table 55, the delay amount data storing unit 56, the determination table 74 and the determination table 83 may be provided outside the image pickup device drive mode selecting unit 91.

Then, a user can select an arbitrary one function from among the functions of the image pickup device drive mode selecting unit 54, the image pickup device drive mode selecting unit 73 and the image pickup device drive mode selecting unit 82 in the image pickup device drive mode selecting unit 91, by, for example, operating a selection switch 30*a* provided in a selecting unit 30.

The present modification provides the first embodiment further including: insertion portion length obtaining means for obtaining information on a length of an insertion portion 2; exposure information obtaining means for obtaining exposure information from an image picked up by the image pickup device arranged in the distal end portion 6 of the insertion portion 2; the acceleration sensor 71 provided in the insertion portion 2, the acceleration sensor 71 obtaining information on a motion of the insertion portion 2; blurring detecting means for detecting blurring information based on at least two images picked up by the image pickup device; first image pickup device drive mode selection means for selecting an image pickup device drive mode stored in advance in first storing means, based on the length information outputted from the insertion portion length obtaining means and the exposure information outputted from the exposure information obtaining means; second image pickup device drive mode selection means for selecting an image pickup device drive mode stored in advance in second storing means, based on the information on the motion of the insertion portion 2 outputted from the acceleration sensor 71; third image pickup device drive mode selection means for selecting an image pickup device drive mode stored in advance in third storing means, based on the blurring information outputted from the blurring detecting means; and the selection switch 30*a*, which is selection means for a user to select one image pickup device drive mode selection means from among the first image pickup device drive mode selection means, the second image pickup device drive mode selection means and the third image pickup device drive mode selection means, and the control circuit 22 sets one image pickup device drive mode from among first to third image pickup device drive modes based on the image pickup device drive mode selected via the selection switch 30*a*.

According to the present modification, a user can freely select one image pickup device drive mode selection means the user wishes from among three image pickup device drive mode selection means, and properly set an image pickup device drive mode using the selected image pickup device drive mode selection means. In addition to that, the present modification has operations and effects of the first embodiment. Note that the selection switch 30*a*, which is selection means, may be provided outside the selecting unit 30.

Although in FIG. 19, one image pickup device drive mode selection means can be selected from three image pickup device drive mode selection means, one image pickup device drive mode selection may be selected from two image pickup device drive mode selection means. Also, although the description has been provided in terms of a case where the configuration in FIG. 19 is applied to the first embodiment, the configuration may also be applied to the second embodiment or the third embodiment.

The above embodiments (including the modifications) have been described in terms of cases where the first drive mode provides a drive frequency that is higher than that in the second drive mode, settings may be made so as to provide the opposite.

Also, although the description has been provided for the case of two different drive frequencies, settings may be made so that three or more drive frequencies can selectively be employed to drive an image pickup device such as the CCD 9. Also, two different drive frequencies or three or more different drive frequencies may be set in a variable manner according to the number of pixels in an image pickup device such as the CCD 9. Also, other embodiments may be configured by, e.g., partially combining the above-described embodiments.

What is claimed is:

1. An endoscope apparatus comprising:
    an image pickup device including an effective pixel region to be used for display and an ineffective pixel region not to be used for display, in order to pick up an image of an object;
    a signal transmission cable disposed inside an insertion portion, the signal transmission cable transmitting an output signal of the image pickup device;
    an analog front-end circuit that receives an input of the output signal of the image pickup device transmitted via the signal transmission cable, and samples the output signal and converts a resulting output signal into a digital signal;
    a signal processing circuit that performs signal processing on the output signal of the image pickup device inputted via the analog front-end circuit, and outputs a first horizontal transfer clock having a predetermined frequency and a second horizontal transfer clock having a frequency that is different from the frequency of the first horizontal transfer clock;
    a timing generator that in order to read out information in the effective pixel region of the image pickup device in an image pickup device drive mode that is either of two different first and second image pickup device drive modes, receives an input of either the first horizontal transfer clock or the second horizontal transfer clock, and upon receipt of an input of the first horizontal transfer clock, generates a first image pickup drive signal based on the first horizontal transfer clock in the first image pickup device drive mode, and upon receipt of an input of the second horizontal transfer clock, generates a second image pickup drive signal based on the second horizontal transfer clock in the second image pickup device drive mode; and
    a control circuit that controls operation of the timing generator and the signal processing circuit,
    wherein when the image pickup device drive mode for reading out the information in the effective pixel region of the image pickup device is switched from the first image pickup device drive mode to the second image pickup device drive mode, the control circuit performs control so that a change is made to the frequency of the second horizontal transfer clock for the timing generator to generate the second image pickup drive signal during a period from a start of transfer of pixel information in the ineffective pixel region of the image pickup device after completion of transfer of pixel information in the effective pixel region of the image pickup device until an output of a next vertical synchronization signal, and then output the vertical synchronization signal.

2. The endoscope apparatus according to claim 1,
    wherein the timing generator includes one image pickup drive signal generating circuit that generates the first image pickup drive signal and the second image pickup drive signal according to the first and the second horizontal transfer clocks, respectively, and one pulse generating circuit that outputs an analog front-end pulse to the analog front-end circuit; and
    wherein the analog front-end circuit includes one analog front-end circuit that samples the output signal of the image pickup device driven by the first image pickup drive signal and the output signal of the image pickup device driven by the second image pickup drive signal, respectively, and converts resulting output signals into digital signals, using the analog front-end pulse.

3. The endoscope apparatus according to claim 1,
    wherein the timing generator includes
    a first timing generator including a first image pickup drive signal generating circuit that generates the first image pickup drive signal, and a first pulse generating circuit that outputs a first analog front-end pulse to the analog front-end circuit for the output signal of the image pickup device where the image pickup device is driven by the first image pickup drive signal, and
    a second timing generator including a second image pickup drive signal generating circuit that generates the second image pickup drive signal, and a second pulse generating circuit that outputs a second analog front-end pulse to the analog front-end circuit for the output signal of the image pickup device where the image pickup device is driven by the second image pickup drive signal; and
    wherein the analog front-end circuit includes one analog front-end circuit that samples the output signal of the image pickup device and converts a resulting output signal into a digital signal, using the first or second analog front-end pulse.

4. The endoscope apparatus according to claim 1,
    wherein the timing generator includes
    a first timing generator including a first image pickup drive signal generating circuit that generates the first image pickup drive signal, and a first pulse generating circuit that outputs a first analog front-end pulse to the analog front-end circuit for the output signal of the image pickup device where the image pickup device is driven by the first image pickup drive signal, and a second timing generator including a second image pickup drive signal generating circuit that generates the second image pickup drive signal, and a second pulse generating circuit that outputs a second analog front-end pulse to the analog front-end circuit for the output signal of the image pickup device where the image pickup device is driven by the second image pickup drive signal; and wherein the analog front-end circuit includes a first analog front-end circuit that samples the output signal of the image pickup device where the image pickup device is driven by the first image pickup drive signal and converts a resulting output signal into a digital signal, using the first analog front-end pulse, and a second analog front-end circuit that samples the output signal of the image pickup device where the image pickup device is driven by the second image pickup drive signal and converts a resulting output signal into a digital signal, using the second analog front-end pulse.

5. The endoscope apparatus according to claim 3 further comprising a stop control circuit that stops operation of the first and second timing generators, wherein the stop control circuit sets only the first timing generator that generates the first image pickup device drive mode that is selected in normal time, into an operating state, upon provision of an instruction for an image pickup device drive mode change, the stop control circuit starts the second timing generator that generates the second image pickup device drive mode corresponding to the change, and then makes the image pickup device drive mode change to the second image pickup device drive mode, and after the image pickup device drive mode change to the second image pickup device drive mode, the stop control circuit stops the operation of the first timing generator.

6. The endoscope apparatus according to claim 4, further comprising a stop control circuit that stops operation of the first and second timing generators, wherein the stop control circuit sets only the first timing generator that provides the first image pickup device drive mode that is selected in normal time, into an operating state, and upon provision of an instruction for an image pickup device drive mode change, the stop control circuit starts the second timing generator that provides the second image pickup device drive mode corresponding to the change, and makes the image pickup device drive mode change to the second image pickup device drive mode, and after the image pickup device drive mode change to the second image pickup device drive mode, the stop control circuit stops the operation of the first timing generator.

7. The endoscope apparatus according to claim 1, further comprising a selecting unit that makes a selection of a movie or a still image to display an image signal generated by signal processing in the signal processing circuit in an image pickup device drive mode of the first and the second image pickup device drive modes, the image pickup device drive mode providing a lower drive frequency, wherein the control circuit performs control so as to display the output signal where the image pickup device is driven by the image pickup device drive mode that provides the lower drive frequency, on a display unit in a form of a movie or a still image according to a selection made by the selecting unit.

8. The endoscope apparatus according to claim 1, further comprising a mode change switch for changing the image pickup device drive mode, the mode change switch being operated by a user, wherein the control circuit sets one image pickup device drive mode from the first and second image pickup device drive modes, based on a state of the mode change switch being operated.

9. The endoscope apparatus according to claim 1, further comprising:

an insertion portion length obtaining circuit that obtains length information on a length of the insertion portion;

an exposure information obtaining circuit that obtains exposure information from an image picked up by the image pickup device arranged in a distal end portion of the insertion portion; and an image pickup device drive mode selecting circuit that selects a preset image pickup device drive mode, based on the length information outputted from the insertion portion length obtaining circuit and the exposure information outputted from the exposure information obtaining circuit, wherein the control circuit sets one image pickup device drive mode from the first and second image pickup device drive modes, based on the image pickup device drive mode selected by the image pickup device drive mode selecting circuit.

10. The endoscope apparatus according to claim 1, further comprising:

an acceleration sensor provided in the insertion portion, the acceleration sensor obtaining motion information on a motion of the insertion portion; and an image pickup device drive mode selecting circuit that selects a preset image pickup device drive mode based on the insertion portion motion information outputted from the acceleration sensor, wherein the control circuit sets one image pickup device drive mode from the first and second image pickup device drive modes based on the image pickup device drive mode selected by the image pickup device drive mode selecting circuit.

11. The endoscope apparatus according to claim 1, further comprising:

a blurring detecting circuit that detects blurring information based on at least two images picked up by the image pickup device; and an image pickup device drive mode selecting circuit that selects a preset image pickup device drive mode based on the blurring information outputted from the blurring detecting circuit, wherein the control circuit sets one image pickup device drive mode from the first and second image pickup device drive modes based on the image pickup device drive mode selected by the image pickup device drive mode selecting circuit.

12. The endoscope apparatus according to claim 9, further comprising a timing adjusting circuit that adjusts a timing for outputting an analog front-end pulse to be outputted from the timing generator to the analog front-end circuit, according to the endoscope insertion length information outputted from the insertion portion length obtaining circuit.

13. The endo scope apparatus according to claim 1, further comprising a main body portion provided at a proximal end of the insertion portion, the main body portion including the analog front-end circuit, the signal processing circuit, the timing generator and the control circuit incorporated therein.

14. The endoscope apparatus according to claim 1, further comprising:
an insertion portion length obtaining circuit that obtains length information on a length of the insertion portion;
an exposure information obtaining circuit that obtains exposure information from an image picked up by the image pickup device arranged in the distal end portion of the insertion portion;
an acceleration sensor provided in the insertion portion, the acceleration sensor obtaining motion information on a motion of the insertion portion;
a first image pickup device drive mode selecting circuit that selects an image pickup device drive mode stored in advance in a first storage device, based on the length information outputted from the insertion portion length obtaining circuit and the exposure information outputted from the exposure information obtaining circuit;
a second image pickup device drive mode selecting circuit that selects an image pickup device drive mode stored in advance in a second storage device, based on the insertion portion motion information outputted from the acceleration sensor; and
a selection switch that allows a user to select one image pickup device drive mode selecting circuit from the first image pickup device drive mode selecting circuit and the second image pickup device drive mode selecting circuit,
wherein the control circuit sets one image pickup device drive mode from the first and second image pickup device drive modes based on the image pickup device drive mode selecting circuit selected via the selection switch.

15. The endoscope apparatus according to claim 1, comprising:
an insertion portion length obtaining circuit that obtains length information on a length of the insertion portion;
an exposure information obtaining circuit that obtains exposure information from an image picked up by the image pickup device arranged in a distal end portion of the insertion portion;
a blurring detecting circuit that detects blurring information based on at least two images picked up by the image pickup device;
a first image pickup device drive mode selecting circuit that selects an image pickup device drive mode stored in advance in a first storage device, based on the length information outputted from the insertion portion length obtaining circuit and the exposure information outputted from the exposure information obtaining circuit;
a second image pickup device drive mode selecting circuit that selects an image pickup device drive mode stored in advance in a second storage device, based on the blurring information outputted from the blurring detecting circuit; and
a selection switch that allows a user to select one image pickup device drive mode selecting circuit from the first image pickup device drive mode selecting circuit and the second image pickup device drive mode selecting circuit,
wherein the control circuit sets one image pickup device drive mode from the first and second image pickup device drive modes, based on the image pickup device drive mode selecting circuit selected via the selection switch.

16. The endoscope apparatus according to claim 1, further comprising:
an insertion portion length obtaining circuit that obtains length information on a length of the insertion portion;
an exposure information obtaining circuit that obtains exposure information from an image picked up by the image pickup device arranged in a distal end portion of the insertion portion;
an acceleration sensor provided in the insertion portion, the acceleration sensor obtaining motion information on a motion of the insertion portion;
a blurring detecting circuit that detects blurring information based on at least two images picked up by the image pickup device;
a first image pickup device drive mode selecting circuit that selects an image pickup device drive mode stored in advance in a first storage device, based on the length information outputted from the insertion portion length obtaining circuit and the exposure information outputted from the exposure information obtaining circuit;
a second image pickup device drive mode selecting circuit that selects an image pickup device drive mode stored in advance in a second storage device, based on the insertion portion motion information outputted from the acceleration sensor;
a third image pickup device drive mode selecting circuit that selects an image pickup device drive mode stored in advance in a third storage device, based on the blurring information outputted from the blurring detecting circuit; and
a selection switch that allows a user to select one image pickup device drive mode selecting circuit from the first image pickup device drive mode selecting circuit, the second image pickup device drive mode selecting circuit and the third image pickup device drive mode selecting circuit,
wherein the control circuit sets one image pickup device drive mode from the first to third image pickup device drive modes, based on the image pickup device drive mode selecting circuit selected by the selection switch.

17. The endoscope apparatus according to claim 16, further comprising a timing adjusting circuit that adjusts a timing for outputting an analog front-end pulse to be outputted from the timing generator to the analog front-end circuit, according to the endoscope insertion portion length information outputted from the insertion portion length obtaining circuit, or the image pickup device drive mode.

* * * * *

UNITED STATES PATENT AND TRADEMARK OFFICE
CERTIFICATE OF CORRECTION

| | | |
|---|---|---|
| PATENT NO. | : 9,516,245 B2 | Page 1 of 1 |
| APPLICATION NO. | : 14/536904 | |
| DATED | : December 6, 2016 | |
| INVENTOR(S) | : Yokohama | |

It is certified that error appears in the above-identified patent and that said Letters Patent is hereby corrected as shown below:

Column 29, Line 3 Claim 13, Line 1 should read:
The endoscope apparatus according to claim 1, Signed and Sealed this
Twenty-eighth Day of March, 2017

Michelle K. Lee
*Director of the United States Patent and Trademark Office*